US006627441B1

(12) United States Patent
Attree

(10) Patent No.: US 6,627,441 B1
(45) Date of Patent: Sep. 30, 2003

(54) INCREASING LEVELS OF GROWTH REGULATOR AND/OR WATER STRESS DURING EMBRYO DEVELOPMENT

(76) Inventor: Stephen M. Attree, 749 Byng Street, Victoria, British Columbia (CA), V8S 5B1

(*) Notice: Subject to any disclaimer, the term of this patent is extended or adjusted under 35 U.S.C. 154(b) by 0 days.

(21) Appl. No.: 09/325,935

(22) Filed: Jun. 4, 1999

(30) Foreign Application Priority Data

Jun. 5, 1998 (CA) .............................................. 2240135

(51) Int. Cl.[7] .............................. C12N 5/00; C12N 5/02; A01H 11/00; A01H 9/00; A01H 5/00
(52) U.S. Cl. ..................... 435/422; 435/420; 435/430.1; 435/410; 800/295; 800/298
(58) Field of Search ................................. 435/420, 422, 435/430.1, 410; 800/295, 298

(56) References Cited

U.S. PATENT DOCUMENTS

| | | | | |
|---|---|---|---|---|
| 5,036,007 A | * | 7/1991 | Gupta et al. | ............ 435/240.45 |
| 5,187,092 A | * | 2/1993 | Uddin | ...................... 435/240.5 |
| 5,464,769 A | * | 11/1995 | Attree et al. | .............. 435/240.4 |
| 5,506,136 A | * | 4/1996 | Becwar et al. | ......... 435/240.49 |
| 5,731,191 A | * | 3/1998 | Rutter et al. | .............. 435/430.1 |
| 5,731,203 A | * | 3/1998 | Handley, III | .............. 435/430.1 |
| 6,022,744 A | * | 2/2000 | Tetteroo et al. | ............. 435/410 |

OTHER PUBLICATIONS

Attree, S. M., Rennie, P. J., and Fowke, L. C., "Inducation of Somatic Embryogenesis in Conifers" in Plant Tissue Culture Concepts and Laboratory Exercises, Trigiano, R. N. and Gray, D. J., eds. New York: CRC Press, 1996 pp 191–192.*

Xin, Y. L., Huang, F. H. and Gbur, E. E. Jr. Polyethylene Glycol–Promoted Development of Somatic Embryos in Loblolly Pine (*Pinus taeda* L.) In Vitro Cell. Dev. Biol.— Plant 33: 184–189 Jul./Aug./Sep. 1997.*

Attree, S. M., M. K. Pomery and L. C. Fowke "Development of white spruce (*Picea glacua* (Moench.) Voss) somatic embryos during culture with abscisic acid and osmoticum, and their tolerance to drying and frozen storage" Journal of Experimental Botany, Vol.*

Attree et al, Journal of Experimental Botany, vol. 46, No. 285, pp 433–439, Apr. 1995.*

Dunstan et al. (1988), *Effects of abscisic acid and analogues on the maturation of white spruce (Picea alba)*, Plant Science 58: 77–84.

Dunstan et al. (1991), *Racemic abscisic acid and abscisyl alcohol promote maturation of white spruce (Picea glauca) somatic embryos*, Plant Science 76: 219–228.

Taylor et al. (1991), *Triacyl glycerol bioassembly in microspore–derived embryos of Brassica napus L. cv. Reston*, Plant Phys. 97: 65–79.

* cited by examiner

*Primary Examiner*—Bruce R. Campell
*Assistant Examiner*—Anne Marie Grunberg
(74) *Attorney, Agent, or Firm*—Michael Best & Friedrich; Lisa C. Childs; Brian J. Lum

(57) ABSTRACT

The invention comprises methods for producing mature desiccated and desiccation-tolerant somatic embryos, particularly conifer embryos. The methods include the application of a growth-promoting hormone such as abscisic acid (ABA) to the immature embryos during development. The embryos are also water stressed during development. The concentration of the ABA undergoes a net increase relative to its initial concentration to reach a peak prior to discontinuing ABA treatment when the embryos have attained a moisture content of between 32 and 55%. The water stressing may remain constant or may undergo a net increase in intensity over the period of time during which it is applied to the embryos. The method may optionally include the further water stressing of the mature embryos to further reduce moisture contents of the embryos preferably to the level at which the embryos are tolerant of freezer storage.

94 Claims, 4 Drawing Sheets

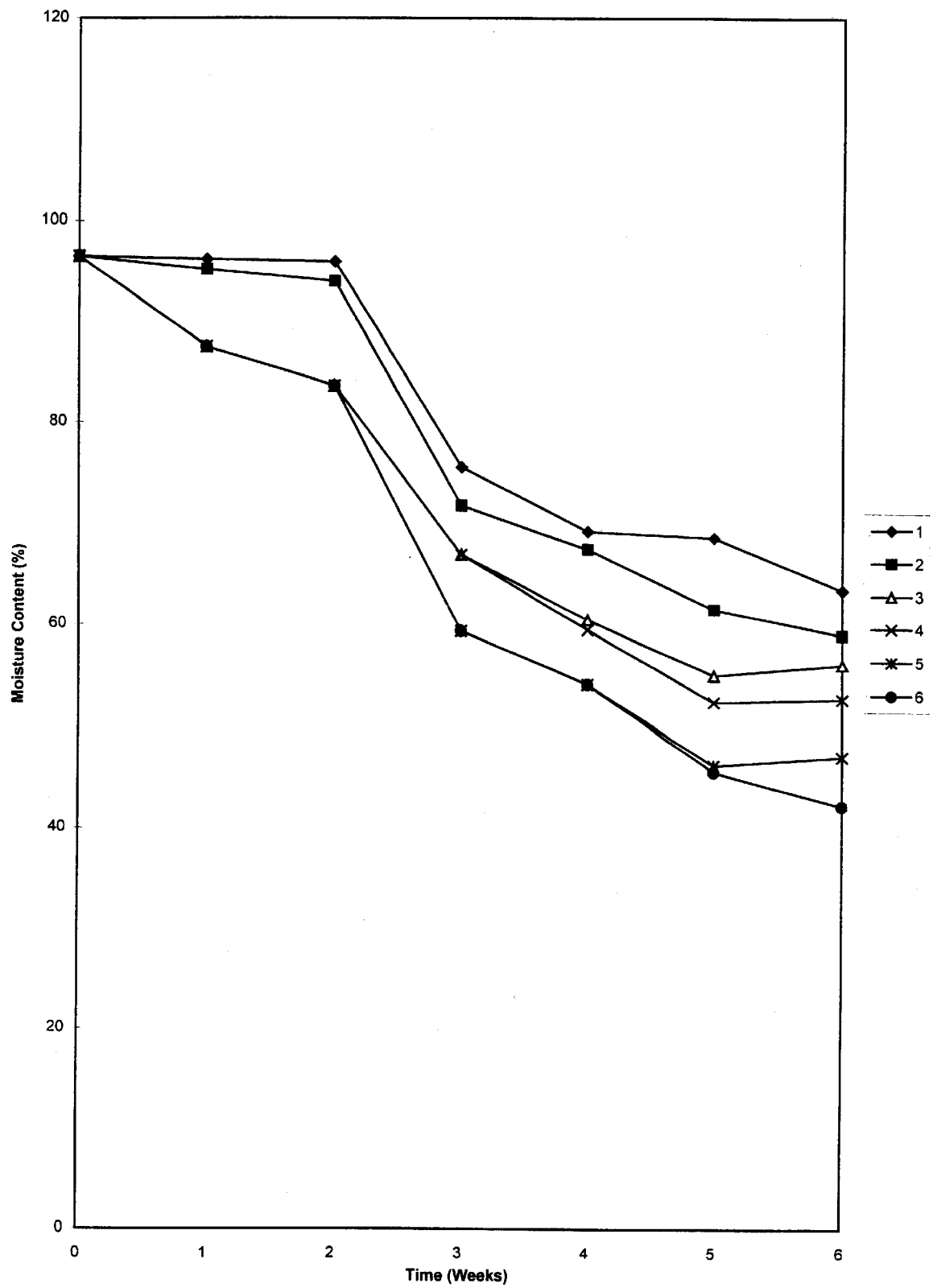
Figure 1. Effect of osmoticum, osmolality and ABA concentration on moisture content of white spruce somatic embryos during development.

Figure 2. Effect of Replacing PEG with Sucrose or Lactose during Development on Maturation Frequency
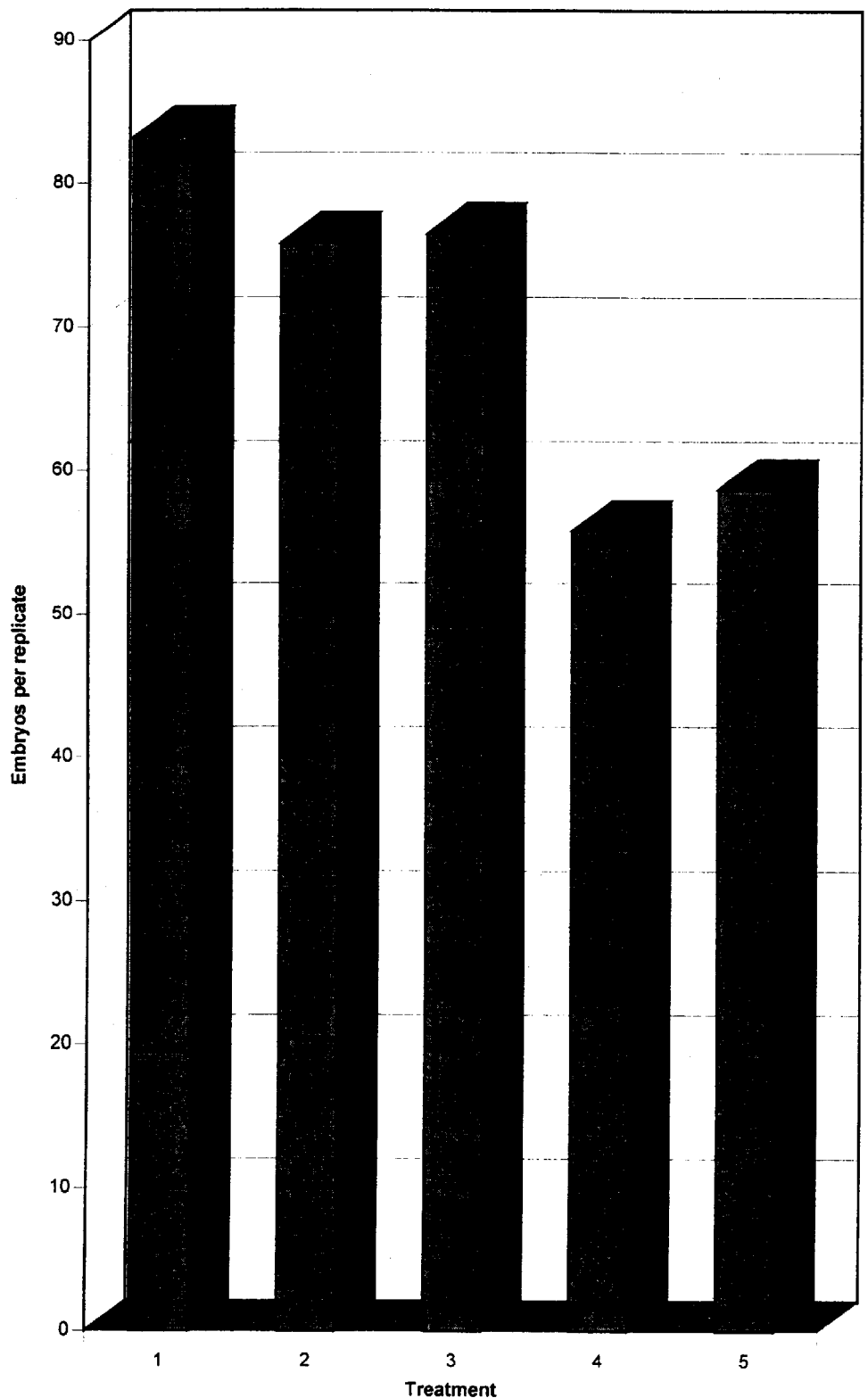

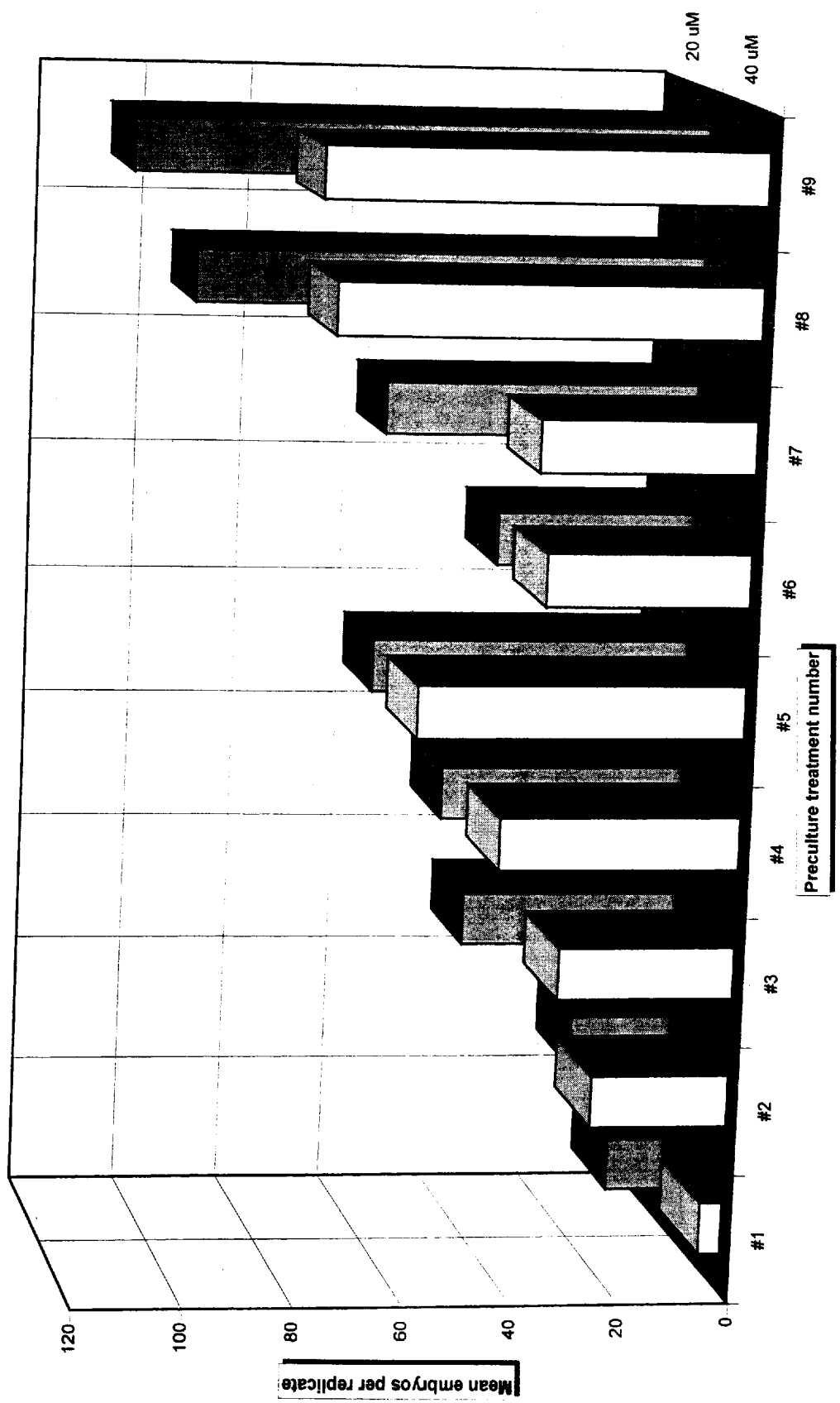
Figure 4. Effect of ABA concentration on development frequency of white spruce somatic embryos following various preculture treatments

INCREASING LEVELS OF GROWTH REGULATOR AND/OR WATER STRESS DURING EMBRYO DEVELOPMENT

CROSS-REFERENCE TO RELATED APPLICATION

This application claims priority from Canadian Patent Application No. 2,240,135 filed Jun. 5, 1998.

FIELD OF THE INVENTION

This invention relates to a development treatment for somatic embryos, particularly conifer embryos, including water stressing and growth regulator treatment, preferably including the use of a relatively high molecular weight non-permeating osmoticum and abscisic acid or equivalents, characterized by an increase in the concentration of the growth regulator or the intensity of the water stressing during the course of the growth regulator treatment.

BACKGROUND OF THE INVENTION

Somatic embryogenesis offers the potential to produce clonally large numbers of plants of many species at low cost. Somatic embryos, develop without the surrounding nutritive tissues and protective seed coat found in zygotic embryos, so considerable research has been devoted to causing somatic embryos to functionally mimic seeds with regard to efficient storage and handling qualities. The development of techniques for somatic embryogenesis in conifers has greatly improved the ability to culture conifer tissues in vitro and now offers the means to propagate clonally commercially valuable conifers of a number of species. However, there is still room in the technology for improvement of the quality and vigour of plants resulting from somatic embryos, including those from all species of conifers.

It has been suggested to use abscisic acid (ABA) or osmoticum or both for enhancing storage levels in plant cells. For example, it was shown that somatic embryos of Theobroma cacao could be induced to accumulate fatty acids approaching the composition of commercial cocoa butter by using a high sucrose concentration in the culture medium (Pence et al. 1981; Physiol. Plant. 53:378–384). Modifying the culture conditions by osmoticum concentration and/or ABA content similarly improved lipid accumulation in *Brassica napus* L. somatic- (Avjioglu and Knox 1989; Ann. Bot. 63:409–420) and microspore-derived (Taylor et al. 1990; Planta 181: 18–26) embryos as well as somatic embryos of carrot (Dutta and Appelqvist 1989; Plant Sci. 64: 167–177) and celery. Also, the level of storage lipids in *P. abies* somatic embryos was improved by optimizing the ABA level to between 10–20 $\mu$M, but the somatic embryos contained about 4% of the lipid level obtained by zygotic embryos (Feirer et al. 1989; Plant Cell Rep. 8:207–209).

Japanese laid-open patent publication No. 1-218520, issued on Aug. 31, 1989, describes a process for producing plant body regenerative tissue. The process includes a step of cultivating a plant body regenerative tissue in a medium containing ABA and having an osmotic pressure of 180 to 2500 mmol/kg. In-order to control the osmotic pressure within the specific range, a non-toxic substance such as sugar, alcohol, an amino acid or glycol is added.

Water stress plays an important role in maintaining embryos in a maturation state (Kermode 1990, Crit. Res. Plant Sci. 9, 155–194). Kermode suggests that low water content rather than ABA prevents precocious germination during later stages of development. This is important because precocious germination of embryos during development in seeds would be lethal during desiccation.

A conventional way to water stress plant cells grown in vitro is to increase the osmotic concentration of the culture medium through the use of plasmolysing osmotica. For example, increased concentrations of plasmolysing osmotica such as sucrose have been used to promote somatic embryo maturation of many plant species. Sucrose at levels of 3 to 6% was found to improve somatic embryo development of many conifers (Attree and Fowke 1993). It seems that high concentrations generally led to repressed embryo development. Mannitol had a similar effect on maturation of conifer somatic embryos (Roberts 1991; Physiol. Plant. 83; 247–254). Low levels of mannitol (2–6%) led to a doubling of the number of mature embryos recovered at the end of the maturation period; however, the treatment could only be applied as a short pulse (one week) as prolonged maturation treatment with mannitol became detrimental to further embryo maturation.

Poor embryo response using sucrose and mannitol or other simple sugars and salts may be due to the absorption of such plasmolysing, osmotica by the symplast of plant cells. Such absorption facilitates adjustment of tissue osmotic potential (osmotic recovery) without lowering the tissue water content. Additionally, direct or indirect metabolic effects on specific plant metabolites can occur, due to utilization of the solute by the embryo or its toxic effects.

Alternatives to plasmolysing osmotica are non-plasmolysing osmotic stresses as well as other forms of non-plasmolysing stresses which have the same effect as drought conditions. Such stresses can be induced using a controlled environmental relative humidity (r.h.) or, for example, by non-permeating high molecular weight compounds such as polyethylene glycol (PEG) or dextran. These compounds are usually available in a wide range of molecular weights. For example, PEG is available in molecular weights ranging from 200 to 35,000. However, only those with a molecular weight above 1000 would normally be considered to be non-permeating. This is because the large molecular size of these solutes excludes their passage through plant cell walls, so preventing entry into cells and consequently preventing plasmolysis, while still removing water (Carpita et al, 1979). Consequently, their non-plasmolysing effect reduces tissue water content in a manner similar to the effects of water stress observed in cells of plants subjected to drought conditions. The effect is constant and cell turgor can only be restored by cells actively increasing their cellular solute concentrations. PEG has been most commonly used to apply water stress to whole plants, to osmotically prime whole seeds to synchronise germination and improve seedling vigour.

Embryo drying occurs naturally in most seeds, and has a role to play in the developmental transition between maturation and germination. Thus, desiccation leads to enhanced germination of both zygotic and somatic embryos. Desiccation of whole somatic embryos is also an alternative method of germplasm storage. Somatic embryos produced continuously year-round could therefore be dried and stored until the appropriate planting season, or shipped to new locations.

A number of prior patents and publications describe methods for the desiccation of somatic embryos. In U.S. Pat. No. 4,615,141 issued on Oct. 7, 1986, Janick and Kitto describe a method for stimulating desiccation. tolerance to asexual plant embryos which are then desiccated. In this method, the embryos are removed from medium containing auxin and cytokinin to a hormone-free development medium. During subsequent development, the somatic embryos are pre-treated by increasing the sucrose concentration of the development medium from normal levels to high levels, or by applying ABA. The hydrated embryos are then encapsulated in a hydrated coating material. The coating material dries to form a thin, non-toxic film enclosing one or more embryos, protecting the embryos during storage but readily redissolving in an aqueous solution. The use of ABA and increased sucrose during embryo development is suggested to improve subsequent survival of the encapsulated embryos during desiccation. Once the embryos have been encapsulated, they are dried at a temperature ranging from 20 to 30° C. for a period of at least five hours.

In U.S. Pat. No. 4,777,762 Oct. 18, 1988, Redenbaugh et al. describe a method for producing desiccated analogs of botanic seeds which are created by providing ABA during the development phase then removing a portion of the water by slow or fast drying so that the plant tissue is no longer saturated with water. The method also involves encapsulating meristematic tissue in a hydrated gel or polymer and removing water by slow or fast drying. The formation of somatic embryos is induced and the embryos are then encapsulated in the gel or polymer followed by drying. Alternatively, the somatic embryos are desiccated to less than complete tissue saturation during, or at the end of, embryo development and then encapsulated.

McKersie et al. (U.S. Pat. No. 5,238,835, issued on Aug. 24, 1993), describe a method through which in vitro formed plant embryos are desiccated following the application of ABA or other types of environmental stress inducing desiccation tolerance. The embryos are induced at the torpedo-shaped stage or later with the source of ABA for a sufficient period of time to cause expression of desiccation tolerance. The induced embryos are then dried to provide stable, viable artificial seeds.

McKersie et al. emphasize the importance of stimulating the embryo at the appropriate stage by the use of signals to develop tolerance to desiccation. It is stressed that if the signals are applied at the incorrect stage of development, the tissue will not respond properly. Angiosperm embryos can undergo maturation in the absence of ABA, and it is suggested that ABA be supplied as late as possible during the maturation protocol and applied for a relatively short period of time. Hence, the timing and duration of ABA application seem to be critical.

Japanese laid-open patent publication. No. 2-031624, issued on Feb. 1, 1990, discloses the use of ABA in plant cultures. ABA is used as part of a process for drying embryos prior to storage.

Senaratna et al., in 1989, Plant Science, 65, pp. 253–259, describe the induction of desiccation tolerance in alfalfa somatic embryos by exogenous application of ABA in the form of a short pulse. Embryos are then dried to 10 to 15% of their moisture content and stored for at least three weeks in the dry state. Senaratna et al. also describe a method by which tolerance to desiccation is induced by exposing the somatic embryos to sub-lethal levels of low temperature, water, nutrient or heat stress prior to desiccation. However, it was demonstrated that some of these stress pre-treatments had deleterious effects on embryo maturation and seedling vigour.

Hence, the prior literature on somatic embryos, and artificial seeds shows that desiccation tolerance was achieved in some plant species such as alfalfa, geraniums, celery, brassica, carrots, corn, lettuce, orchard grass and soybeans. Various methods were suggested, which all appear to revolve around promoting desiccation tolerance by applying ABA and other stresses late in maturation and subsequently reducing the water content of the embryos. However, these methods were not applicable to all species including conifers.

Conifer somatic embryos appear to be different from the somatic embryos of monocotyledonous and dicotyledonous species in that ABA should be supplied as early as possible, to conifer embryos in maturation protocols in order to promote embryo maturation. Merely reducing or eliminating auxin and cytokinin levels, as has been successful for maturation of somatic embryos of many angiosperm species (Ammirato 1983, Handbook of Plant Cell Culture, Vol. 1, pp. 82–123) leads to infrequent or poor maturation in conifer embryos and more often results in browning and death of the immature somatic embryos. Furthermore, it appears that ABA should be applied for longer periods and at higher levels than generally applied to angiosperm somatic embryos in the past.

In U.S. Pat. No. 5,183,757, Roberts (issued on Feb. 2, 1993) describes a process for assisting germination of spruce somatic embryos that comprises partially drying the embryo at humidities of less than about 99.9%. Roberts also suggests that a medium having a sucrose concentration of 2 or 3.4%, which is used between the maturation treatments and the germination media, promotes root and shoot elongation. Roberts mentions that the humidity range that can be used for partial drying of somatic embryos without lethal effect is about 85 to 99.9%, which according to the Roberts method results in only a very small (5–10%) moisture loss.

In a study published in Can. J. Bot., Vol. 68, 1990, pp. 1086–1090, Roberts et al. mention that conifer somatic embryos do not survive desiccation at room humidity, but that partial drying at very high humidity promoted germination up to 90% (as opposed to the 95% to 100% germination described in the examples of the present invention detailed below). Roberts et al. also refer to the fact that drying embryos over a range of r.h. indicated that r.h. of 81% or lower was lethal to conifer embryos. This can be further visualized at Table 3 of the report where the effects of partial drying at different r.h. on germination are shown. It can be seen that very small levels of germination are obtained following drying at a r.h. of 90% and that no germination is observed when r.h. of 81% and 75% are used. Based on those results, Roberts et al. conclude that only a mild drying of the somatic embryos was possible to permit normal germination and that the spruce somatic embryos do not tolerate desiccation to zygotic levels. According to Roberts et al., spruce somatic embryos did survive and undergo improved vigour following a partial drying treatment in an environment of very high humidity (over 95% humidity), during which time only 5% of moisture was removed.

Later, Roberts et al. (J. Plant Physiol., 138, pp. 1–6, 1991) emphasize that somatic embryos from a number of species, including spruce, are sensitive to severe water loss and show decreased survival following desiccation. In this paper, Roberts shows that Sitka spruce somatic embryos do not survive desiccation, even though high frequency and synchronised germination could be obtained following partial drying of the embryos.

Hence, despite attempts to desiccate conifer somatic embryos following ABA maturation, survival was not described until Attree et al (U.S. Pat. No. 5,464,769, issued on Nov. 7, 1995). The important aspect of the invention of Attree et al. resided in the combined use of a non-plasmolysing water stress and ABA during the embryo maturation process to stimulate maturation frequencies and promote further maturation of the embryos, and to increase dry weight and lower moisture content, leading to desiccation tolerance to moisture contents below 36%. Constant levels of ABA were maintained during development of the embryos. With regard to the non-plasmolysing water stress, a non-plasmolysing high molecular weight compound such as PEG having a molecular weight range over 1000 (e.g., PEG 4000) or other high molecular weight polymers such as dextran having a minimum molecular weight over 7000 was preferred, although other non-plasmolysing water stresses such as increased gel strength, or environmental stresses were also suggested. Attree et al. in WO 93/11660 suggest that when using bioreactors for development the environment could be controlled and ABA and water stress levels raised or lowered at the start or end of maturation.

PEG has been included in conifer embryo maturation protocols with varying success. For example, Ilic-Grubor et al., in, pending U.S. patent application Ser. No. 09/096,547 (filed on Jun. 12, 1998), disclose that, in some circumstances, using PEG as a water stress in the presence of a restricted carbon source may enhance embryo development. In the specific context of conifers, Norgard 1997 (Plant Science 124, 211–221) and Li et al. 1997 (In Vitro Cell. Dev. Biol.-Plant 33, 184–189) report that PEG has a positive effect on maturation, while others found negative effects on maturation and germination (Cornu and Geoffrion 1990, Euk. Soc. Bot. Fr. 137, 25–34; Gupta et al., U.S. Pat. No. 5, 036,007; Klimaszewska et al. 1997 Can. J. For. Res. 27, 538–550; Find 1977, Plant Science 128, 75–83.

There has been a trend for using increasingly higher concentrations of ABA to promote the maturation of conifer somatic embryos, probably resulting from a need to inhibit precocious germination late in maturation which has become more apparent following the increasingly longer maturation times used. Thus, ABA was first successfully used by Hakman and von Arnold 1988 (Physiol. Plant. 72:579–587) and von Arnold and Hakman 1988 (J. Plant Physiol. 132:164–169), at 7.6 $\mu$M. Dunstan et al. 1988 (Plant Sci. 58:77–84) subsequently found 12 $\mu$M ABA to be better. Shortly after, Attree et al. 1990 (Can. J. Bot. 68:2583–2589) reported that 16 $\mu$M was optimal. Roberts et al. 1990 (Physiologia Plantarum 78; 355–360) have shown that for some species of spruce, ABA at 30–40$\mu$M could be used to promote maturation and yield mature embryos with storage protein polypeptides comparable to zygotic embryos. Such high levels were necessary to prevent precocious germination and allow maturation to proceed to later stages. Dunstan et al. 1991 (Plant Sci. 76:219–228) similarly found that high levels could permit embryo maturation. Unfortunately, high ABA levels used throughout the development period also increased the frequency of developmentally abnormal embryos. In the above reports concerning conifers, increased osmoticum or water stress was not included with the ABA. Recently, much higher ABA concentrations have been described. Becwar et al., U.S. Pat. No. 5,506,136, issued on Apr. 9, 1996, describe ABA in development media at levels up to 120 $\mu$M. Dunstan et al., 1997 (Journal of Expt. Bot. 48, 277–287) suggest that a remedy to prevent precocious germination of conifer somatic embryos is to transfer cultures to fresh medium with ABA in the maturation culture period, as is commonly done. It is stated that exposure to fresh ABA is unlikely to lead to greatly improved yields of mature somatic embryos, unless the population of immature embryos remains sizable, but is more likely to lead to improvement in the quality of the mature somatic embryos through deposition of storage product and prevention of precocious germination. Dunstan et al.1997 (J. Plant Physiol.) show that the availability of (+)-ABA decreases during culture, which can lead to precocious germination. They suggest that this is generally attributed to a low concentration of ABA, and also that extending the use of ABA during the maturation phase by periodic transfer to fresh nutrient medium would extend ABA availability. Uddin 1993 (U.S. Pat. No. 5,187,092, issued on Feb. 16, 1993) describes using various combinations and proportions of glucose, maltose, abscisic acid and/or indolebutyric acid to promote maturation of conifer somatic embryos. This patent suggests that conifer somatic embryos should be cultured in the presence of maltose and/or glucose in a total concentration of at least 3%, and at least 10 $\mu$M ABA. A two-step process is described in which the preferred concentration of maltose is 6% and the ABA is raised preferably after about four weeks culture from 20 $\mu$M to 30 $\mu$M. Uddin provides no information on why ABA was raised and whether raising ABA was preferable to maintaining constant ABA, or reducing it in the presence of the permeating osmoticum. It is not disclosed in the patent whether the embryos obtained by means of the Uddin method were viable and capable of vigorous germination. Kapik et al. 1995 (Tree Physiology 15, 485–490), and Kong et al., 1997 (Physiologia Plantarum 101, 23–30) show that endogenous ABA rises during seed and zygotic embryo development then falls during late development. Therefore, the current thinking is that ABA should not be increased, or even maintained at a constant level during development, but should be moderately high at the start of development then decreased throughout development to low levels or to zero at the end of the culture period, promoting germination.

Thus, in U.S. Pat. No. 5,034,326, Pullman et al. (Jul. 23, 1991) describe a method for developing tissue culture-induced coniferous somatic embryos into well-developed cotyledonary embryos. The method comprises a multi-stage culturing process in which early stage embryos are cultured on a late stage medium comprising a significantly higher osmotic potential along with moderately high ABA and an absorbent material to gradually, reduce the level of available ABA over time. A critical aspect of this method lies in the inclusion of the absorbent material in the embryo development medium. Absorbent materials suggested include activated charcoal and silicates. The absorbent is used to slowly reduce the ABA and remove metabolic waste products. The purpose of this reduction in ABA is to follow the natural tendency in embryo development. Pullman et al. suggest that as development approaches completion, the presence of lesser amounts of ABA is required.

Similarly, Gupta et al. in U.S. Pat. No. 5,036,007 (Jul. 30, 1991) describe a similar method. In Douglas fir culture, ABA is reduced from about 10–20 $\mu$M at the start of development to less than about 3 $\mu$M or even to zero. The method also suggests the use of osmotica to control osmotic potential. A preferred osmoticum suggested is sucrose in amounts in the range of 2 to 3%. Another osmoticum that is suggested by Gupta et al. is PEG. Gupta et al. mention that PEG 8000 was evaluated and found to be a superior osmoticum in the presence of decreasing ABA levels, stating that the reasons for its superior performance compared with other materials is not entirely clear. Gupta et al. also suggest that polyethylene or polypropylene glycols of other molecular weights are believed to be equally useful. According to U.S. Pat. No. 5,036,007, the combination of osmotica is to be modified at some point during the development stage. In fact, the patent teaches that the osmotic concentration is increased during development in conjunction with the decrease in ABA. If development is started at levels around 300–350 mmol/kg, the osmotic level may be increased during development to a final level of about 450 mmol/kg.

A similar method was described in U.S. Pat. No. 5,236,841, issued on Aug. 17, 1993, by Gupta et al.; however, the described technique relates to the use of gradually decreasing amounts of the abscisic acid during the time when the embryos are further developed into cotyledonary embryos by stepwise subcultures. It was suggested that when transfers to fresh medium are made, the initial ABA level of the fresh medium should not be higher than the final level of the medium at the end of the preceding culture period. In examples in which activated charcoal was used, exogenous ABA levels were required to be an order of magnitude higher due to the ability of charcoal to rapidly absorb ABA.

More recently, however, Gupta et al. in U.S. Pat. No. 5,482,857 (Jan. 9, 1996) have found that, when using activated charcoal, ABA was not necessary for cotyledonary embryo development of Douglas fir. Similar methods to those above are also described in the more recent patents by Pullman and Gupta (U.S. Pat. No. 5,294,549, Mar. 15, 1994) and Gupta (U.S. Pat. No. 5,563,061, Oct. 8, 1996). The aforementioned U.S. Pat. Nos. 5,294,549, 5,563,061, and 5,236,841 all suggest that it is advantageous to use one combination of osmotica at the beginning of development and transfer embryos to a medium having a different combination during development. In U.S. Pat. No. 5,036,007, Gupta et al. also suggest the replacement of PEG with an alternative osmoticum such as lactose or sorbitol mid-way through development as embryos tended to deteriorate over time in the presence of PEG. Similarly, U.S. Pat. Nos. 5,731,191 and 5,731,204 (both issued on Mar. 24, 1998) report that the use of PEG throughout development was found to cause a "germination block". To overcome this "germination block", these patents teach the use of PEG for only the first part of development and the use of a cold treatment during development, respectively. U.S. Pat. No. 5,731,203, also issued on Mar. 24, 1998, teaches the avoidance of the use of PEG altogether, and instead teaches the use of high levels of ABA throughout development.

Desiccation of conifer somatic embryos is desirable to enable somatic embryos to be stored for very long periods. Storage times of desiccated embryos may be further extended by storing frozen embryos. The ability to survive prolonged storage is important given the long life cycles of conifers and the length of time required to evaluate in vitro produced trees. Tissues able to survive freezing in liquid nitrogen are considered to be capable of survival following storage for indefinite periods. Dronne et al. 1997 (Physiologia Plantarum, 99:433–438) recently showed that desiccation decreases abscisic acid content in hybrid larch somatic embryos, which is consistent with the earlier understanding of abscisic acid as an inhibitor of precocious germination.

In conclusion, most available techniques within the prior state of coniferous somatic embryo development technology have failed to provide optimally vigorous and viable conifer somatic embryos and especially, viable desiccated conifer somatic embryos, although the previous Attree et al. work mentioned above has carried the technology forward considerably. Conifer somatic embryos require particular combinations of hormonal and water stressing conditions in order to develop. Current methods call for the application of moderate to high levels of ABA to be applied at the start of development, then for the application of fresh medium in which exogenous ABA is maintained at a constant level in order to control precocious germination at the end of development, or in which ABA is decreasing from the point at which it is first applied, or is even absent throughout development in order to attempt to match the zygotic pattern of ABA levels. In the latter method, precocious germination is controlled by increasing the osmotic concentration of the medium. High levels of ABA have been reported to lead to developmental abnormalities, while high levels of osmotica have been shown in some instances to be detrimental. Decreasing ABA and sub-optimal water stress teaches away from the conditions required for successful desiccation tolerance. Therefore, applying high levels of ABA throughout development, or decreasing ABA, in association with permeating osmotica is not desirable for conifers. More suitable methods for culturing plant embryos are therefore required.

Moreover, some prior reports suggest that water stressing using an osmoticum, or particular osmotica, is unreliable, at least over certain moisture content reduction ranges. The poor response with osmoticum, and PEG in particular, reported by some possibly results from a number of factors, such as unduly prolonged exposure to PEG/ABA, inadequate desiccation or inadequate removal of endogenous ABA prior to germination, sub-optimal PEG/ABA levels during culture, incorrect preparation of PEG/ABA media, incompatible gelling agents or incompatible molecular weight of PEG, and incorrect combinations of osmotica. As shown in the Examples detailed below, when media are prepared correctly, ABA and water stressing may be increased to very high levels towards the end of development, which can lead to superior embryo quality showing that non-plasmolysing water stressing at correct levels for at least a substantial part of development in combination with optimal levels of ABA is most suitable for conifer embryos.

SUMMARY OF THE INVENTION

The invention comprises methods of culturing immature somatic embryos in the presence of a growth regulator and water stressing to produce mature desiccation tolerant somatic embryos. The somatic embryo culturing processes of the present invention are similar in their objectives and steps to the various processes described in prior allowed U.S. patent application Ser. No. 08/244,725 (Attree et al.) filed on Aug. 18, 1994 and allowed on Jun. 20, 1997, counterpart to pending Canadian patent application Serial No. 2,125,410 filed on Dec. 18, 1992, but differ in that the present invention is characterized by increasing concentrations of growth regulator or intensities of water stressing during the course of development and produces higher yields of higher quality desiccation-tolerant embryos, which convert (that is, exhibit, both needle development and a viable root) into somatic seedlings with improved vigour compared to those resulting from production methods known previously.

The invention comprises three principal variants, the common characteristic of which is that the level of stress hormone growth regulator (such as abscisic acid or its precursors, derivatives, or analogs) or the intensity of the water stressing applied to the embryos over a selected period of time is raised during the development (maturation) of the immature embryos to the late cotyledonary stage. As timing is relevant to both the growth regulator and water stressing treatments, it is to be understood that, unless otherwise stated, the early part of embryo development refers to the period from the immature/suspensor stage to the globular stage, the middle refers to the period from the club-shaped stage to the early cotyledonary stage, and the late part of development is the remaining period in which the cotyledons become fully developed. Of course, these are not exact definitions, and it is to be understood as well that there is often significant overlap between these periods.

In this description, such terms as "ABA" and "ABA treatment" encompass any of the family of stress hormone growth regulators such as those mentioned in the preceding paragraph, or treatment by such growth regulators, as the case may be. The mature somatic desiccation-tolerant embryos produced in accordance with the methods of this invention may be desiccated to low moisture contents (which are indicated herein as a percentage of total embryo weight), preferably to moisture contents low enough to permit the embryos to survive freezing, and/or stored for extended periods of time, and/or germinated to produce somatic seedlings of high quality and good vigour. A further aspect of the invention is that the application of exogenous abscisic acid (ABA) to the embryos may be commenced at a suitable selected time during the development/maturation of the immature embryos, the selection of the commencement time depending upon such variables as the species and genotype being cultured, the length of the maturation culture period, the initial concentration of ABA, and other applicable factors. Additionally, the water stressing may also commence at a suitable time, selected with regard to the aforementioned factors, during the development/maturation of the immature embryos, although the commencement of the ABA application and the commencement of the water stressing do not have to coincide.

In accordance with the first two variants, the ABA treatment preferably commences at some point from the immature suspensor stage to the club-shaped stage, and the concentration of the exogenous ABA is progressively increased as the development of the immature embryos progresses, preferably to a cotyledonary stage although the application of ABA may be discontinued prior to the attainment of that stage. Ideally, the increase in ABA concentration would be continuous, however, it is expected that in practice the increase will be effected in a stepwise or incremental fashion. In the context of the present invention, the preferred progressive increase in exogenous ABA concentration refers to the general upward trend of ABA concentration levels over time, which encompasses the possibility of interim declines or plateaus in the ABA concentration curve relative to time, as well as ever-increasing concentration of exogenous ABA.

In accordance with a first variant of the invention, the water stressing does not increase in intensity during development. Alternatively, in accordance with a second variant, the immature somatic embryos are cultured in the presence of a suitable water stress and ABA, the intensity of the water stressing as well as the concentration of the ABA increasing during the development period. However, it is not necessary to correlate (i) the duration of the increasing water stressing, (ii) the timing of the increase of water stressing, or (iii) the magnitude of the increase of water stressing with the counterpart parameters applicable to the increase of the ABA concentration. As the embryos are susceptible to developmental abnormalities if excessively high water stress is exerted upon the embryos too early in development, the second variant of the invention provides the advantage of increasing yields of mature desiccation-tolerant embryos associated with high rates of embryo water loss without severe risk of causing developmental abnormalities including precocious germination. Finally, in accordance with the third variant, the level of ABA remains substantially constant while the intensity of the water stressing increases over the course of development. As in the context of the increasing ABA, the increase in water stressing contemplated in the second and third variants is ideally continuous, but is expected to be effected in a stepwise fashion, and encompasses the possibility of plateaus and declines punctuating the general upward trend. In any of these variants of the invention, it is advantageous to discontinue the application of exogenous ABA or remove the exogenous ABA prior to the embryos' attainment of moisture contents of less than about 30%, and preferably when the embryos reach between about 55% and about 30% moisture content, although the discontinuance or removal may be effected prior to the attainment of about 55% moisture content.

All of these variants tend to produce substantially increased yields of mature, fully developed somatic embryos (as defined below), with high desiccation tolerance and improved vigour relative to embryos produced in accordance with previously known methods, while late, unwanted embryogenic tissue proliferation (that can occur in the absence of somatic embryo maturation) and precocious germination are prevented or inhibited.

Immature somatic embryos that have been cultured in the presence of a suitable water stress and ABA, in accordance with either of the first two variants discussed above, may then be subjected to severe water stressing (desiccation) to low moisture content, which severe water stressing may occur either in the presence or absence of culture medium, depending on how the embryos are desiccated. The desiccated mature embryos produced by this modification may have moisture contents as low as about 5–10%, and preferably at least low enough that the embryos are sufficiently devoid of unbound water to permit them to tolerate being frozen and stored. Moisture content levels of such embryos are usually less than about 36% at the. upper limit of the range. Such desiccated embryos may be stored indefinitely at a range of storage temperatures, from about room temperature to very low temperatures approaching about −200° C., and a relatively high percentage of such embryos are subsequently typically able to germinate to produce vigorous plantlets. As a very high water stress too early in development is detrimental and causes embryo abnormalities, it is preferable that the intensity of the water stressing during the development time period contemplated in the first two variants of the invention be lower than that of the water stressing exerted upon the embryos to severely desiccate them once they have reached the desiccation-tolerant stage.

Although low-intensity water stressing of at least about −0.1 MPa may be employed in preculturing the embryos (along with hormone levels that are, reduced from those initially used to induce somatic embryogenesis, such as about a tenth or less of the concentrations of auxin and cytokinin), water potentials for the development treatment per se can range from −0.3 MPa at the start of the water stressing treatment to preferably between about −100 to −500 MPa at the end of desiccation. The term "water stressing" includes stressing the embryos by subjecting them to low water potential drought conditions (such as a relative humidity environment, higher relative osmotic pressure (such as by the inclusion of osmotica in the substrate upon which they are grown), and any other forms of water stress (moisture stress) that tend to lower the moisture content of the embryos. Non-plasmolysing water stressing is preferred, although under some circumstances (notably as the embryos become increasingly mature), the embryos are to a greater extent resistant to potentially plasmolysing water stress that at an earlier stage of development might lead to sufficiently severe plasmolysis to kill the embryo. It is to be understood that, in addition to non-permeating osmotica and environmental stress, non-plasmolysing water stressing may be effected by, inter alia, permeating osmotica at sufficiently low concentrations to avoid plasmolysis of the embryonic cells. That is, any concentration of a metabolizable carbon source that exceeds the amount of nutrient which is utilized by the embryos for nutrition will have an osmotic effect which exerts water stress upon the embryos. For example, even a 3% concentration of sucrose may be sufficient to exceed embryos' nutritional needs and exert a water stress, while being sufficiently low (see, for example, Ilic-Grubor et. al., supra) to avoid causing permanent developmental damage by plasmolysis. Moreover, it is to be understood that non-plasmolysing water stressing encompasses water stressing that may cause some relatively minor reversible plasmolysis from which the embryos are able to recover while suffering little reduction of their overall viability and vigour. Although the lower the moisture content of the embryos, the higher the concentration of permeating osmotica necessary to cause plasmolysis, non-permeating osmotica are still preferred as the primary means of water stressing the embryos during at least the early part of development, as such osmotica are prevented or impeded from entering the cells, thereby reducing toxic effects. Permeating osmotica can be applied later in development, when the embryonic cells have already lost some of their moisture and are less likely to be susceptible to irreversible plasmolysis. As osmotica having sizes of about 30 Angstrom units (Å) or more cannot pass through the cell wall, this is the minimum size of the preferred non-permeating osmotica. In this respect, polyethylene glycol (PEG) is suggested as a suitable water stressing agent, which can be substituted by any other suitable polyalkylene glycol, or alternatively by any other suitable high-molecular-weight water stressing agent. The preferred minimum molecular weight of PEG to be used in accordance with this invention is about 1000. Gels may also provide a non-permeating water stress; for example, 1% or higher w/v PHYTAGEL™ is suitable for water stressing. Moreover, it is not necessary to use only one means of water stressing throughout the development period and/or further water stressing period; rather, the means used may be varied. As relative water stress levels or intensities may not admit of easy quantitative determination, an empirical results-oriented approach may be taken; if following a particular water-stressing treatment it appears that the embryos were not optimally water-stressed to reach a particular target moisture content and target viability percentage, the water-stressing environment may be suitably modified, as by varying the amount of osmoticum, the composition or relative drying effect of gel in the medium, the relative humidity in the vicinity of the embryos, any other water stressing applied to the embryos, or the time during which any particular water-stressing effect is applied.

For embryo nourishment during development, a suitable metabolizable carbon source is preferably restricted to less than about 90 mM (or about 3%) for sucrose and equivalent well-metabolised carbon sources, but this is not essential. Moreover, it is noted that both the metabolizable carbon source(s) and other components of the medium may increase the relative osmotic pressure of the medium.

In any of the foregoing alternative processes according to the invention, the exposure of the embryos to one or both of ABA and water stress should preferably begin by the time the embryos reach the globular stage, although it may begin as early as the immature (i e., suspensor) stage, and continue through the club-shaped stage to the early and late cotyledonary stages. It is to be understood that the water stressing of and/or application of ABA to the embryos may be interrupted or decreased at any time, as long as there is a net increase in the level of exogenous ABA at any point prior to the final discontinuation of the ABA application (in the case of the first two variants described above) or, in the third variant, in the intensity of water stressing prior to the end of the water stressing treatment. After the ABA treatment is discontinued, it is preferable to continue to water stress the embryos to a severely desiccated state (that is, to moisture contents less than about 30% to 36%), during which the exogenous ABA drops to low levels or to zero. Such severe desiccation promotes survivability following long-term embryo storage and tends to render the embryos freezer storage-tolerant.

It is not necessary to apply the ABA and water stress to the embryos concurrently, nor is it necessary to raise the levels of one or both of these factors consistently throughout the process. However, both should preferably be at relatively higher levels later in culture, such as at or near the end of culture, prior to the point of the removal or discontinuance of exogenous ABA and/or water stress. Preferably both ABA and water stressing should be increased throughout the early cotyledonary stages of development. The magnitude of the increase of either the ABA concentration or of the intensity of water stressing may be as little as about 5% above the initial level, but may also be many times higher than the initial level, depending on the species chosen and the initial level of the ABA or water stressing that is applied. In the discussion of increases in intensity of water stressing, the incremental increase relates to the increase in the magnitude of the water potential, which in turn relates to the rate of embryo water loss. Thus, if the initial water potential is, say, −100 MPa, a 5% increase in the intensity of water stressing would result in the water potential decreasing to −105 MPa. In this specification, "increasing" or "raising" water potential means increasing the absolute value of the numerical value expressed, regardless of whether the value is expressed in positive or negative terms. For the purposes of this discussion, a mature embryo (that is, one having successfully reached the end of development) may be defined as having full desiccation tolerance, having a moisture content of less than 55% (preferably between about 30% and 55%), and having achieved the late cotyledonary stage and being capable of developing into a plant. However, it is to be noted that further changes occur during desiccation that enhance the vigour of the desiccated embryos, relative to those mature embryos that are not water stressed to low moisture contents.

It can be understood from, the foregoing discussion that two variants of this invention comprise a method for producing viable mature conifer somatic embryos comprising water stressing the somatic embryos, preferably beginning earlier than the globular stage, in medium containing ABA whose concentration in medium increases during development, including such increase towards the mid-point of cotyledonary development of the embryos when the tendency for precocious germination is the highest, prior to the water content of the embryos becoming sufficiently low to inhibit precocious germination. (At low moisture content of the embryos below about 40%, the embryos naturally resist precocious germination, so any further increase in ABA levels beyond such stage of desiccation of the embryos is unhelpful; ABA treatment may normally cease at such stage.) Water stressing also begins during development, although it does not have to coincide with the timing of the initial application of exogenous ABA. In one variant of the method of the invention, the water stressing is maintained at a substantially constant level during its application, in order to maintain a substantially constant water potential which, in turn, causes the reduction of the embryos' water content at a substantially constant rate. Preferably, water stressing continues at least to the end of the development period, although it may be discontinued prior to that point. Desiccation of the embryos may then be carried out.

As mentioned, also contemplated within the scope of the invention is an alternative method in which the intensity of water stressing (and therefore the magnitude of the water potential, which is discussed further-below) rises throughout development and in which ABA concentrations also rise during the period of ABA application. Finally, the third alternative method is that in which the intensity of the water stressing rises throughout development while the ABA concentration remains constant throughout the ABA treatment period. Preferred ABA concentrations for all of the alternatives discussed thus far may be in the range of 0.1 $\mu$M to 200 $\mu$M.

In accordance with the first two (rising-ABA) variants, the preferred initial concentrations are in the range 1–40 $\mu$M (although higher concentrations may be used in some instances), and more preferably 5–30 $\mu$M, which then increase during development to a peak of preferably about 30–60 $\mu$M. Concentrations of ABA greater than 100 $\mu$M later in development may be preferable in some instances, as will be described below. The increase can be at any developmental point or throughout development. At the uppermost level, ABA should be present at a concentration of 30–300 $\mu$M or possibly even higher, but most preferably 30–100 $\mu$M. Moreover, as variables such as the quality, purity, and source of ABA as well as the presence of an adsorbent also bear upon the effectiveness of the exogenous ABA on bringing about the desired embryonic development activity, an empirical approach may require that concentrations even higher than about 300 $\mu$M be used in accordance with this invention. Activated charcoal or some other adsorbent may be used to remove toxic compounds from the medium; however, as an adsorbent for toxins would also tend to absorb exogenous ABA, the ABA levels must be increased sufficiently to maintain a net increase of exogenous ABA during the increasing-ABA phase of the invention. (As will be discussed in more detail below, ABA may be maintained at constant levels at the beginning or the end of development, and may also be reduced somewhat at the end.)

In any variant, to circumvent unwanted adsorption of ABA during treatment of the embryos, the selected adsorbent may be first saturated with ABA prior to addition to the culture, to inhibit ABA absorption during embryo development while still permitting removal of toxins. Alternatively, filtration systems such as, dialysis or molecular sieves may be used instead of adsorbents to remove toxins, in such a manner as to maintain the net increase of ABA during the increasing-ABA phase of the invention. (In addition, dialysis membranes and molecular sieves may fulfill other functions, such as to provide physical support to the embryos while allowing the embryos access to nutrients in media and to lessen or prevent the contact of the embryos with toxins that may otherwise play a useful role in the culture, such as, for instance, high molecular weight osmotica that may have a toxic effect if in contact with the embryos.) Frequent replacement of the medium when increasing ABA can also serve tolerance toxins. Of course, it is to be understood that more than one toxin removal means may be used in combination or in series.

Also within the scope of the invention are methods of the foregoing character involving increasing-ABA (which, as already mentioned, includes increasing equivalent growth regulator) treatment or increasing-water stressing of the somatic embryos in combination with subsequent desiccation of the somatic embryos to a moisture content of less than about 40%, and preferably less than about 30%. Embryos having moisture contents of less than about 30% may be considered fully desiccated, although embryos having moisture contents of as low as about 5–10% may survive storage and germinate successfully. In this last modification of the methods in accordance with the invention, moderately low ABA and water stress (e g., less than about 30 $\mu$M ABA, with the concentration of non-permeating PEG (polyethylene glycol) adjusted to provide a water potential of the medium of less than about 350 mmol/kg, and preferably in the range of 250–350 mmol/kg) are preferably applied within the first 1–4 weeks of the maturation culture. In variants in which the ABA is to be increased, it is preferably increased up until about the point of the development period when the embryos are. entering the early to mid-cotyledonary stages.

The increase of ABA and/or water stress from the initial (non-zero) levels to the final desired levels can be accomplished in multiple steps of whatever increment the user prefers, or in one transfer. The increase in ABA, may be effected, for example, by medium replacement or by simply adding concentrated ABA to the medium to effect the. final desired rise in ABA. To be most effective, exogenous ABA should preferably rise throughout the majority of the early- to mid-culture period so that ABA levels are high close to the end of development, particularly at the mid to late cotyledonary stage. Subsequent additions of ABA provide the conditions required at the middle stages of culture suitable for suppressing precocious germination, promoting development and providing optimal desiccation tolerance late in development. It is not necessary to apply ABA in one step to high levels at the start of development and then continuously decrease the levels throughout development, as has been suggested in the prior art. As discussed, the magnitude of the incremental increase may be as little as 5% of the initial level to as much as many times the initial level, depending on the species to which the embryo belongs and the initial level of ABA or water stress that is chosen. Moreover, the incremental increases in ABA concentration do not have to remain the same, rather the increments may be varied. By way of example, the first incremental increase may be 5% of the initial ABA concentration, while the second increase may be 7% or 10% of the initial ABA concentration. Thus, a graphic representation of the period during which ABA concentration is increased does not necessarily have to be a straight line nor an approximation of same. In addition, the concentration of ABA may be maintained at the initial level over some duration of the development period, prior to being raised, and the uppermost concentration of ABA may similarly be maintained at that level over time. There may even be some drop from the uppermost concentration to the final concentration of ABA in the development period (effected in one or more incremental reductions) as long as there is a net increase in exogenous ABA concentration from the commencement to the discontinuation of ABA application.

Although somatic embryos may be cultured on gelled medium, bioreactors, which are highly suitable for use with liquid medium and so me types of which allow the relative humidity to be controlled, may be used, as the one practising the method will presumably apply understanding already well known in the technology, including the modification of the medium during development, e g., in the manner for medium replacement effected in a bioreactor as described by Attree et al. (1994, Plant Cell Rep, 13:601–606). The change in levels of exogenous ABA causes changes in the embryos' endogenous ABA levels, thus effecting the desired developmental changes that are analogous to those occurring naturally in the development of zygotic embryos. Prior to the application of the exogenous ABA, endogenous ABA levels may be as low as zero, although there is usually some naturally-occurring endogenous ABA. In the method of this invention, as exogenous ABA is applied to the embryos, endogenous levels rise. It is not usually necessary to begin increasing the exogenous concentration of ABA until the increase in levels of endogenous ABA is desired. The concentration of endogenous ABA peaks at around the mid-cotyledonary stage, after which it begins to fall again as the embryos' moisture contents decrease. Without limiting the generality of the foregoing, it is preferred that, over a given time period in the growth regulator treatment, smaller and more frequent increases of ABA concentration be applied to the embryos rather than larger and less frequent increases. For example, three applications of 10 $\mu$M increases is preferable to one application of a 30 $\mu$M increase over the same time period.

It appears that it is necessary to reduce or eliminate ABA only near the end of development or after development, and preferably when moisture contents are in the range of 30–55%, particularly when further desiccating to less than 30% moisture content. It is desirable that the application of exogenous ABA be restricted to the initial levels or discontinued altogether before the embryonic moisture contents approach about 30% to 36%, as the continued application of a high concentration of exogenous ABA may in some instances raise endogenous ABA thereby inhibiting the proper germination of the desiccated embryos. However, the application of exogenous ABA may be restricted or discontinued prior to this point, and should preferably be restricted or discontinued during the late cotyledonary stages (although it may be done even earlier). In terms of moisture contents, the restriction or discontinuation of exogenous ABA may preferably occur when the embryos have attained a 40% moisture content, or a 55% moisture content or higher. As mentioned earlier, the tendency for precocious germination decreases as the embryo moisture content decreases, such that the germination-inhibiting effect of ABA becomes unnecessary at low enough moisture contents. As the desirable influence of ABA is therefore ineffective when the embryos no longer tend to germinate precociously, the completion of the ABA treatment may coincide with the natural inhibition of precocious germination. Likewise, the completion of the ABA treatment may be brought about by the removal of the embryos from the germination-inhibiting influence of ABA. It is therefore to be understood that some ABA may even remain in contact with embryos at the completion of the ABA treatment, as long as the remaining ABA is insufficient or unnecessary to adversely inhibit germination.

The discontinuance of ABA application may be effected in one step by the complete removal of the maturation medium from the embryos, or in several steps, for example as the ABA in the medium is successively diluted to zero, as the embryos are transferred to fresh medium with progressively lower. ABA concentrations, or with the addition of an adsorbent such as activated charcoal to the medium. As contemplated in the preferred modification of the three variants, water stressing continues after the restriction/discontinuance of exogenous ABA application, in order to desiccate the embryos further. It is to be understood that water stressing for further desiccation may. also be interrupted or otherwise modified prior to completion. Embryos may undergo the growth regulator treatment on supports in medium, at the end of which the embryos may be removed with their supports from the medium and then desiccated on the supports, or removed from supports and placed on fresh supports wetted with a solution of ABA at the final concentration. During desiccation, the embryos and their supports dry together, thereby restricting the amount of available exogenous ABA. Alternatively, the medium may be completely removed from the embryos, which may then be dried.

During development, it is preferable to maintain a substantially non-plasmolysing water stress until a fully desiccated embryo is obtained. Furthermore, providing a rapid rise to water potentials of high magnitude together with a rapid rise in ABA very early in maturation prior to meristem development and early cotyledon development may be the cause of developmental abnormalities during late stage development, and consequently may result in embryos of poorer quality and fewer mature embryos overall. Equally, one should try to avoid overstressing the embryos; better results are obtained if the embryos are given adequate time to respond to the changes in their environment. Initially, at the beginning of development, the application of moderate to low ABA (e.g., less than about 40 $\mu$M ABA, and preferably about 5–30 $\mu$M), and moderate water stress, preferably comprising a non-permeating component of water potential of less than about 350 mmol/kg, and preferably in the range of 250–350 mmol/kg or less, is most preferred. Non-permeating PEG present in the medium is suitable to apply the water stress. Alternatively, the water stressing may be applied to the embryos in the form of environmental stressing (by, for example, controlling the relative humidity of the culture vessel to provide the requisite level of water stress), or in the form of physical or chemical stress (by, for example, the application of relatively firm gels), or a combination of any of the foregoing.

If the concentration of ABA is to be raised in accordance with the invention then, during development, the ABA concentration should be increased over at least a portion of the development period. In the case of conifer somatic embryos, the ABA should preferably be increased prior to the last few weeks of development, that is, when the embryos have reached the cotyledonary stages. In such instances, the ABA should be increased to about 30 to 200 $\mu$M ABA or even higher, most preferably to 30 to 100 $\mu$M ABA.

In accordance with either the second or third preferred variant of the invention involving increasing water stress along with either increasing or constant growth regulator, respectively, the water stress preferably should be increased prior to the last few weeks of development, that is, prior to the time when the embryos have reached the cotyledonary stages, and most preferably throughout development from the immature suspensor stage, through the globular and, in gymnosperm embryos, club stages, to the cotyledonary stage. The water stressing during these stages should preferably be non-plasmolysing (which, of course, may include permeating osmotica at non-plasmolysing concentrations). For example, the absolute value of the magnitude of the water potential should rise to about 800 mmol/kg or greater, preferably to about 400–700 mmol/kg, and most preferably to about 500–600 mmol/kg.

The novel combinations of increasing ABA with a constant level of water stressing, increasing the intensity of water stressing with a constant concentration of ABA, and increasing both the intensity of water stressing and the concentration of ABA during development produces high frequencies of mature desiccation-tolerant embryos from initially immature embryos, promotes the development of normal looking somatic embryos (including those of conifer species), and inhibits precocious germination of these embryos.

Mature embryos obtained from the processes leading to desiccation tolerance according to the invention may be germinated directly, or because of desiccation tolerance, may be further desiccated in accordance with the further desiccation option of the invention, which may lead to further improvement in plant vigour. The further desiccation preferably occurs in the absence of a replenishing source of ABA. Water potentials during desiccation may typically reach −100 to −500 MPa to desiccate the embryos to moisture contents below about 30%, although embryo moisture contents may fall to as low as 5% or even less. Preferably the somatic embryos are desiccated after maturation to a moisture content at which there is no unbound water (so that the somatic embryos may be frozen and stored), which is usually below about 30–35%, at which moisture content water potentials preferably are less than about −2 to −2.4 MPa. Fully desiccated somatic embryos may then be germinated or stored indefinitely and then germinated.

Desiccation to low moisture contents may not always be necessary or desired. Desiccation in the absence of exogenous ABA naturally reduces endogenous ABA levels, thereby promoting germination vigour, however, alternative methods to reduce high endogenous ABA may be employed or combined with desiccation, such as stratification of embryos at low temperature, osmotic priming treatments, or ABA inhibitors. Alternatively, such methods may not be required if, for example, the endogenous ABA levels fall with moisture content levels regardless of whether exogenous ABA is being applied. The development times may also be varied to enhance desiccation tolerance, or to compensate for development temperature variations, development time requirements for different species, and so forth. Varying the development temperatures, by, for example, culturing at lower temperature or using a high/low temperature fluctuation, would lead to longer development times; the principles of the present invention would continue to apply, but one would have to take into account the slower expected reaction time of the embryos at lower temperatures to changes in ambient conditions and other effects that low temperatures might incur. For example, the preferred temperature range in which to develop the embryos is: from about 0° C. to about 35° C., although the range of about 0° C. to about 12° C. may be suitable for at least part of development. Similarly, some species such as pines develop slower than other species such as spruces, so that, for example, instead of employing a six- to seven-week development period that may be used with spruces, a nine- to fifteen-week period may be necessary or desirable for pines. The temperature for desiccation may also be varied preferably between the ranges of 0–35° C. (and most preferably between about 0–12° C.), as might the relative humidity at which desiccation occurs. Environmental or physical methods for desiccation may be employed, and the rate of desiccation may be varied. Mature somatic embryos may be desiccated and/or converted into artificial seeds. All these modifications are considered to be within the scope of the present invention. These methods have been found to be advantageous for a range of conifers, such as spruces (white, black, Norway), Douglas fir, lodgepole pine, and western larch, so are considered advantageous for all conifers, including loblolly pine. Mature somatic embryos obtained by means of this invention which are then germinated show increased vigour over those obtained through conventional treatments that omit the preferred procedures of the present invention. Embryos prepared according to the invention undergo rapid shoot development and growth in soil.

The Examples to be detailed below are limited to application of variants of the methods according to the invention to embryos of coniferous species. However, the expected and predicted reactions to the inventive methods of other embryos indicates the broad utility of the inventive methods for somatic embryo development, without a necessary restriction to conifers. In particular, the response of a given embryo to increases in exogenous ABA concentration levels is, based on known response characteristics of both gymnosperm and angiosperm embryos, expected to be parallel for angiosperm and other gymnosperm species to the responses of specific coniferous embryos to ABA concentration increases detailed below in the Examples. Of course, preferred parameters to be selected for any given embryo development project will vary considerably from case to case, depending not only on the embryos selected for development but also on other factors, such as ambient temperature and humidity, choice of growth medium, timing of commencement of development relative to pre-development proliferation of embryos, the target for terminal moisture content, and other aspects of the development conditions, including the type of bioreactor or containment vessel used and the physical characteristics of the support for the embryos within the vessel, and the quantity of embryos being simultaneously developed. As always, an empirical approach will be necessary to optimize the selection of variable parameters.

SUMMARY OF THE DIAGRAMS

FIG. 1. Effect of treatments 1–6, which contain varying osmoticum and medium water potential and ABA concentration as outlined in example 4, on moisture content of developing white spruce somatic embryos.

FIG. 2. Effect of replacing PEG with sucrose or lactose during development on maturation frequency of white spruce somatic embryos.

FIG. 3. Effect of osmotic potential on development frequency of white spruce somatic embryos following various liquid maturation pretreatments.

FIG. 4. Effect of ABA concentration on development frequency of white spruce somatic embryos following various liquid maturation pretreatments.

DETAILED DESCRIPTION OF THE INVENTION

As a general rule, tissue water potential and osmotic potential can be expressed in Pascals, Newtons per square meter, Barr, or millimoles per kilogram. One MPa corresponds to 403.877 mmol/kg, therefore 1 mmol/kg corresponds to 0.002476 MPa. Tissue water potentials by convention are often negative, but can be given as either negative or positive values. Solution water potentials are often expressed as positive values. In this specification, tissue water potentials are typically expressed as positive values while solution water potentials are typically expressed as negative values.

The methods of this invention are in principle applicable to all conifers, but it is to be understood that where species selected are different from those mentioned in the following examples, an empirical approach to embryo development is recommended that will take into account variables in the environment, equipment available, etc. A variety of culture media are suitable for culturing conifer somatic embryos, so the particular choice is not expected to be important. For spruce, methods in this invention were carried out using half-strength Litvay's medium (LM) containing 0.1 mg/L thiamine and pyridoxine and 5 mg/L nicotinic acid. All media except germination media contained 0.4 g/L glutamine and 0.8 g/L casein hydrolysate. Where gelled medium was used, the medium was gelled using gellan gum (at, for example, 0.15 to 0.2%) unless otherwise indicated. Litvay's medium is available commercially (Sigma product no. L4272). For spruce, sucrose is a suitable carbon source for all culturing stages, although other carbon sources such as maltose, glucose or fructose may be used. The immature somatic embryos were cultured on ½ LM containing 1% sucrose and 9 $\mu$M 2,4-dichlorophenoxyacetic acid ("2,4-D") and 4.5 $\mu$M benzyladenine ("BA"). The growth regulators for maintenance medium were added prior to autoclaving, while glutamine and casein hydrolysate were filter sterilized and added after autoclaving.

Under a light microscope, the proliferating embryogenic tissue consists of differentiated immature somatic embryos. The somatic embryos are polarized structures which are organized into a meristematic embryonal region subtended by elongate suspensor cells. Under the influence of auxin and cytokinin (or, of course, functionally analogous plant hormones such as 2,4-D and BA, respectively), the immature somatic embryos continue to proliferate by splitting into two without further development (cleavage polyembryogenesis). Embryogenic cultures are maintained on solid medium to bulk up tissue prior to initiating suspension cultures, and also as a back-up source of tissue for suspension and cryopreserved cultures. Cultures are subcultured to fresh maintenance medium every one to three weeks. Suspension cultures are an ideal source of rapidly growing embryogenic tissue for providing quantities of embryos for large scale maturation, and these are usually sub-cultured weekly.

It is often beneficial to preculture the suspension culture in modified suspension culture medium containing reduced or no auxin and cytokinin. Preculturing usually leads to a dramatic improvement in maturation frequency and embryo quality. For this invention, preculturing is done in medium (such as, for example, half-strength LM) containing 1–3% sucrose (water potential 90–145 mmol/kg) and zero to one-tenth the strength of auxin and cytokinin present in the proliferation medium for one week. For example, white spruce is generally precultured in $\frac{1}{20}$ strength hormones; while Norway spruce and western larch (Larix occidentalis Nutt.) were precultured in hormone-free medium.

Solid or liquid media may be used for maturation. High molecular weight compounds of any species are incompatible, and separate from one another to form a boundary layer. PEG and gelling agents are both high molecular weight compounds that are incompatible and so do not readily mix. Thus, PEG can severely reduce the gel strength of the culture medium, leading to a water-logged appearance of cultures. Best results with PEG will be obtained when using liquid maturation media, which is particularly useful in conjunction with bioreactors to produce mature embryos. The method for successful gelling of solidified media requires that the PEG should not be of very high molecular weight. Thus, PEG of 8000 and greater should preferably not be used with gelled media. Instead, PEGs of 1500 to 4000 are most suitable for use in gelled media. Also, PEG solutions can be prepared and autoclaved separately from the media salts and gelling agent, then mixed after autoclaving. Agar is less compatible with PEG than gellan gums such as PHYTAGEL™. When prepared correctly, PEG 4000 of up to 20% (w/v) can be used successfully in PHYTAGEL™. Poor gelling results in lack of osmotic control leading to poor embryo quality and vitrification, as was observed by Klimaszewska and Smith 1997, who used PEGs of up to 12,000 molecular weight in gelled media.

For maturation, the ½ LM basal medium was supplemented with 250 mg/L glutamine and 500 mg/L casein hydrolysate and 3% sucrose. Amino acids were filter sterilized and added to cooled media. ABA (Sigma A 2784) stock solutions were prepared by first dissolving ABA in concentrated NaOH. ABA was added after autoclaving. The purity and source of (+)-ABA can influence results. Purer (+)-ABA would be required in lower amounts. Actual levels need to be determined depending on the source of ABA, the components of the culture medium, and species being studied. The concentrations suggested are provided as guidelines. It is also possible to complement the maturation medium by incorporating auxin and/or cytokinin, or plant growth promoters having auxin-like and cytokinin-like activity. Similarly, gibberellin is in principle also a suitable complementary growth promoter, and an empirical approach taking into account such factors as plant species, environment, and so forth should be used to determine the concentration etc. of gibberellin.

For maturation, the solidified culture medium in 9 cm petri dishes was overlaid with a filter paper support to facilitate transfers to fresh media. Onto this was pipetted 0.75 mL of a 20% suspension of precultured cells resuspended in fresh hormone-free preculture medium with 3% sucrose. Cultures were incubated at 25 ° C. in the dark and transferred to fresh medium every two weeks.

In order to desiccate the somatic embryos, they were transferred on their filter paper supports to an empty petri dish. The lid was replaced and left unsealed to prevent contamination while allowing the moisture to escape from the dish. Somatic embryos were desiccated in a sterile chamber in which sterile air at ambient relative humidity (usually 20–60% r.h.) was passed. Similarly, embryos may be desiccated in one or more controlled gaseous environments of relative humidity, ranging from about 5% to 100%. Desiccation at temperatures of 4–25° C. and 40–60% RH have proved to be very satisfactory. Embryos were usually left two weeks to dry. Desiccated embryos can then be stored, preferably frozen, or germinated directly.

For germination, the somatic embryos upon their filter paper supports were rehydrated on germination medium. This consisted of ½ LM, 2% sucrose, 0.7% agar (Sigma), with no growth regulators, glutamine or casein hydrolysate, in petri dishes or Sigma PHYTATRAYS™. They were either placed directly in a growth room at 23° C. for 1 week in the dark, then placed under light (2 Wm-2) for 20 h photoperiod, or first imbibed on the rehydration medium at 0–12° C. (that is, stratified) in the dark for one to four weeks.

Following shoot development, somatic plantlets can be transferred to soil.

Water potentials were measured for liquid media containing various osmotica at a range of concentrations, which were plotted on a curve. Determinations were made using a vapour pressure osmometer (Wescor). Moisture content determinations were done using methods described previously by Attree et al. (U.S. Pat. No. 5,464,769).

EXAMPLE 1

Optimal ABA and Water Stress for White Spruce Development

Experiments were conducted in order to determine the optimal concentrations of ABA and water stress for optimal maturation frequencies which also inhibit precocious germination. Previous studies showed 8% PEG 4000 as osmoticum with 3% sucrose (which, due to its concentration, acted as an additional osmoticum) and 16 μM ABA were suitable, while lower PEG concentrations reduced the number of embryos produced. Ranges were prepared around these results. Thus, immature white spruce somatic embryos were cultured on medium containing 8, 16, 24, and 32 μM ABA. PEG was included in each of the ABA media adjusted to water potentials of 230, 260, 290, and 320 mmol/kg. Embryos were transferred to fresh medium of the same composition and were cultured for a total of six weeks. The number of embryos per dish were then counted and the appearance of the embryos was recorded. Results are for three to eight dishes per treatment. A total of 2439 mature embryos were recorded.

TABLE 1

Effect of ABA concentration and water potential on mean maturation frequency and precocious germination of white spruce somatic embryos.

| PEG medium water potential (mol/kg) | ABA concentration (μm) | | | | Total of means |
|---|---|---|---|---|---|
| | 8 | 16 | 24 | 32 | |
| 310 | 10.7 greening | 0 | 1.0 no greening | 2.5 no greening | 14.2 |
| 290 | 44.3 green and elongated | 20.1 slight greening | 28.7 slight greening | 8.6 no greening | 101.7 |
| 260 | 53.0 green and elongated | 44.0 greening | 22.8 slight greening | 22.7 no greening | 142.5 |
| 230 | 29.7 green and elongated | 15.6 green and elongated | 28.0 greening | 28.0 slight greening | 101.3 |
| total of means | 137.7 | 79.7 | 80.5 | 61.8 | 359.7 |

From Table 1 it can be seen that the highest numbers of embryos were produced from PEG media at a water potential of 260 mmol/kg together with 8 or 16 μM ABA; however, these levels were inadequate to prevent precocious germination over a six week period. To prevent precocious germination, it was necessary to have at least 24–32 μM ABA together with PEG media adjusted to a water potential of at least 230–260 mmol/kg, but maturation frequencies in these treatments were much lower. Thus, the optimal water potentials at the beginning of development are not suitable for late stage development and vice versa. This suggests that in order to maximize maturation frequencies, water potentials should be adjusted initially to about 260 mmol/kg with ABA at 8–16 μM or slightly higher, then to prevent precocious germination the ABA and/or water potential should be raised during development.

EXAMPLE 2

Effect of Varying ABA and Water Stress on Development of White Spruce

In order to test the above hypothesis, various concentrations of PEG and ABA were tested and modified during development of white spruce somatic embryos.

The starting treatments were prepared as outlined in Table 2.

TABLE 2

Medium water potential and ABA concentration of media.

| Treatment | A | B | C | D |
|---|---|---|---|---|
| PEG medium water potential (mmol/kg) | 260 | 260 | 290 | 290 |
| ABA concentration (μM) | 16 | 24 | 8 | 16 |

The embryos were transferred to fresh medium every two weeks over a six week period. Observations were then recorded. The treatments consisted of the following ABA concentrations and media water potentials, with three replicates per treatment.

1. Control (fresh medium of the same composition)
2. Raise ABA
3. Raise PEG
4. Raise PEG decrease ABA
5. Raise PEG and ABA Results were as follows:

Expt A

| | | |
|---|---|---|
| 1. | Control | green, cotyledon elongation |
| 2. | Raise ABA (24, 32 μM) | slight or no greening |
| 3. | Raise PEG (290, 320 mmol/kg) | greening |
| 4. | Raise PEG (290, 320 mmol/kg), lower ABA (8, 8) | greening, cotyledon elongation |
| 5. | Raise PEG (290, 320 mmol/kg), raise ABA (24, 32 μM) | slight or no greening |

Expt B

| | | |
|---|---|---|
| 1. | Control | greening |
| 2. | Raise ABA (32, 32 μM) | no greening |
| 3. | Raise PEG (290, 320 mmol/kg) | no greening |
| 4. | Raise PEG (290, 320 mmol/kg), lower ABA (8, 8 μM) | greening, cotyledon elongation |
| 5. | Raise PEG (290, 320 mmol/kg), raise ABA (32, 32 μM) | slight or no greening |

Expt C

| | | |
|---|---|---|
| 1. | Control | greening, cotyledon elongation |
| 2. | Raise ABA (16, 24 μM) | greening |
| 2. | Raise PEG (290, 320 mmol/kg) | greening |
| 3. | not done | |

-continued

| | | |
|---|---|---|
| 4. | Raise PEG (12, 14%), raise ABA (16, 24 μM) | none or slight greening |
| Expt D | | |
| 1. | Control | greening, cotyledon elongation |
| 2. | Raise ABA (24, 32 μM) | no greening |
| 3. | Raise PEG (290, 320 mmol/kg) | slight greening |
| 4. | Raise PEG (290, 320), lower ABA (8, 8 μM) | greening |
| 5. | Raise PEG (290, 320), raise ABA (24, 32 μM) | no greening |

In general, precocious germination was inhibited and in some cases prevented by either raising ABA concentration or raising PEG concentration. Raising ABA alone was more effective than raising the osmoticum alone; however, the most effective treatment to inhibit precocious germination was to raise both the ABA and PEG together. Results show in experiment A and B that finishing concentrations of ABA and PEG were too low to totally prevent precocious germination in all treatments. Increasing PEG over the concentration range tested was not sufficient to prevent precocious germination if ABA was declining.

These results suggest that if the starting water potential of 260 mmol/kg PEG with 16 μM ABA is to be used in order to maximize the maturation frequencies, then final PEG water potential should preferably be at least 320 mmol/kg, and final ABA should be at least 32 μM.

EXAMPLE 3

Effect of High Intensity Water Stressing and ABA on Inhibition of Precocious Germination In order to determine if water stress and ABA can completely inhibit precocious germination, the following experiments were performed with white spruce and Norway spruce. Somatic embryos were plated on medium containing PEG adjusted to 290 mmol/kg PEG and 16 μM ABA then either transferred to fresh medium of the same composition every two weeks, or transferred every two weeks to medium containing increasing ABA and PEG as outlined in Table 3.

TABLE 3

Concentrations of ABA and PEG medium water potential used at biweekly transfer.

| | Week | | | | | |
|---|---|---|---|---|---|---|
| | 0 | 2 | 4 | 6 | 8 | 10 |
| PEG (mmol/kg) | 290 | 380 | 540 | 580 | 650 | finish |
| ABA (μM) | 16 | 32 | 40 | 48 | 56 | |

Embryos maintained on 290 mmol/kg PEG and 16 μM ABA started greening during the seventh week and by week 10 the embryos were precociously germinated. Thus, a continuous supply of fresh medium containing fresh ABA was insufficient to prevent precocious germination. The embryos had swollen and turned completely green and cotyledons had expanded. Such germinated embryos were of poor quality as they appeared vitrified, with swollen bases and little evidence of roots. Embryos cultured through the schedule of increasing ABA and PEG showed no evidence of precocious germination. The embryos were large and creamy yellow in colour, and no greening was observed.

EXAMPLE 4

Effect of Water Stress and ABA on White Spruce Somatic Embryo Moisture Contents

Moisture contents can be used to identify embryo quality and precocious germination. High moisture contents late in maturation can promote precocious germination, or mark the onset of precocious germination. A continuously decreasing moisture content during development parallels the development of zygotic embryos. The following experiments were carried out to observe the effect of water stress and ABA on embryo moisture contents.

Embryos were cultured on medium containing 3% sucrose and ABA, with additional osmoticum adjusted to vary water potentials, as shown in Table 4.

TABLE 4

Culture media used to culture white spruce somatic embryos prior to moisture content determinations.

| | | Weeks | | |
|---|---|---|---|---|
| Treatment | | 0–2 | 2–4 | 4–6 |
| 1 | ABA | 20 | 30 | 40 |
| control - 3% sucrose | water potential | 190 | 190 | 190 |
| 2 | ABA | 20 | 30 | 40 |
| Mannitol | water potential | 290 | 400 | 540 |
| 3 | ABA | 20 | 20 | 20 |
| PEG | water potential | 290 | 290 | 290 |
| 4 | ABA | 20 | 30 | 40 |
| PEG | water potential | 290 | 290 | 290 |
| 5 | ABA | 20 | 30 | 40 |
| PEG | water potential | 290 | 400 | 400 |
| 6 | ABA | 20 | 30 | 40 |
| PEG | water potential | 290 | 400 | 540 |

Embryos were cultured for six weeks and moisture contents determined. Determinations for each treatment were made weekly, with three replicates per treatment. 50 embryos per replicate were used. In some instances, particularly for the control with low osmoticum, insufficient embryos were produced. In these cases, the minimum number of embryos used per replicate was thirty. For weeks 0 to 2, the embryos were too small to be used for moisture content determinations, so whole tissue was used instead.

The results are shown in FIG. 1. It can be seen that ABA alone (treatment 1) in the absence of high water stress is insufficient to provide a continuous reduction in moisture content. Thus, even doubling ABA from 20 to 40 μM still resulted in embryos with greater than 60% moisture content after six weeks, which showed evidence of greening. Supplementing this medium with mannitol had little effect on the moisture contents of the somatic embryos which still remained above about 60%; however, greening was prevented. PEG medium at 290 mmol/kg with constant ABA (20 μM, treatment 3) led to lower moisture contents, which fell below 55%; however slight greening of cotyledons was observed on a few embryos. PEG medium at 290 mmol/kg with increasing ABA (treatment 4) showed further slight reductions in moisture content. Increasing ABA to 40 μM while increasing PEG medium water potential to 400 mmol/ kg after week two (treatment 5) caused a further reduction in moisture content. However, the treatment that led to a continuous reduction in moisture content was treatment 6. Continuously raising the water potential to 540 mmol/kg, together with 40 μM ABA, led to moisture contents approaching 40% by the end of the six-week culture period in treatment 6. This treatment consistently yielded 300–350 mature somatic embryos per dish. The moisture content of embryos observed in treatment 6 appears similar to that observed in conifer seeds undergoing natural development (Kong et al. 1997). No greening of somatic embryos was observed in treatments 5 and 6, and embryos of good morphological appearance (long slender shape, well-developed cotyledons) were produced. The non-permeating water stress provided by PEG was much more effective than the permeating water stress provided by mannitol at reducing moisture contents even when present at similar water potentials. ABA can promote reductions in moisture content, particularly when raised during development, but moisture contents are best controlled using a combination of water stress and ABA.

EXAMPLE 5

Norway Spruce Culture

Norway spruce was cultured using the same protocol as developed for white spruce. Thus, somatic embryos from full hormone suspension culture were transferred to hormone-free liquid culture medium (half-strength Litvay's medium, 3% sucrose) for one week, then transferred (0.75 mL of 20% suspension) to maturation medium in petri dishes.

The first medium contained PEG adjusted to 290 mmol/kg and 20 μM ABA. After two weeks, the cultures were transferred on their filter paper supports to fresh medium of the same composition, or to medium containing PEG adjusted to 400 mmol/kg and 30 μM ABA. After a further two weeks (i e., the fourth week of culture), the somatic embryos were transferred either to PEG media at a water potential of 400 mmol/kg and 40 μM ABA, or to PEG medium of 540 mmol/kg and 40 μM ABA. Somatic embryos were also plated on medium containing 20 μM ABA and no PEG.

The Norway spruce was particularly prone to germinating precociously. After six weeks, somatic embryos cultured on medium containing no PEG were green and elongated. Even those on 290 mmol/kg PEG medium and 20 μM ABA were green and some had dark green tips to their cotyledons. Somatic embryos that completed the 400 mmol/kg PEG, 40 μM ABA treatment were yellow with a greenish tinge, while those that completed the 540 mmol/kg PEG, 40 μM ABA treatment were small and white with no evidence of precocious germination.

This experiment demonstrated that raising ABA in combination with raising water stress is suitable for encouraging a high frequency of maturation of Norway spruce while reducing tissue proliferation and inhibiting precocious germination.

EXAMPLE 6

Effect of PEG Replacement During Development of White Spruce Somatic Embryos This experiment was carried out to observe the effect of replacing the non-permeating water stress with a permeating water stress during development. Thus, immature somatic embryos from suspension culture were precultured in 1/20 strength hormone medium for one week then transferred to maturation medium containing 3% sucrose, 20 μM ABA and adjusted to 290 mmol/kg with PEG. They were transferred to fresh medium weekly in which the osmoticum and ABA was increased. For the control (treatment 1) the PEG concentration was increased (as outlined in Example 4, treatment 6). In treatment 2, the PEG remained constant and water potential was increased by adding lactose (treatment 2). In treatment 3, PEG was increased after the first week, then lactose was added at the third and fourth weeks, and in the fifth week PEG was removed and replaced completely with lactose. Treatment 4 was the same as treatment 3, except that sucrose was used in place of lactose. Treatment 5 was similar to treatment 3, except that PEG was replaced with lactose earlier so that PEG was replaced totally by lactose by the fourth week. Total development time was six weeks.

TABLE 5

Medium osmotic treatments for culturing white spruce somatic embryos.

| Treatment | Week 1<br>290 mmol/kg<br>20 μM ABA | Week 2<br>338 mmol/kg<br>30 μM ABA | Week 3<br>380 mmol/kg<br>30 μM ABA | Week 4<br>508 mmol/kg<br>40 μM ABA | Week 5<br>508 mmol/kg<br>40 μM ABA |
|---|---|---|---|---|---|
| 1 Control | 3% sucrose<br>7.5% PEG | 3% sucrose<br>10% PEG | 3% sucrose<br>12.5% PEG | 3% sucrose<br>15% PEG | 3% sucrose<br>15% PEG |
| 2 | 3% sucrose<br>7.5% PEG | 3% sucrose<br>10% PEG | 3% sucrose<br>10% PEG<br>3.32% lactose | 3% sucrose<br>10% PEG<br>6.64% lactose | 3% sucrose<br>10% PEG<br>6.64% lactose |
| 3 | 3% sucrose<br>7.5% PEG | 3% sucrose<br>10% PEG | 3% sucrose<br>10% PEG<br>3.32% lactose | 3% sucrose<br>6.25% PEG<br>8.41% lactose | 3% sucrose<br>10.07% lactose |
| 4 | 3% sucrose<br>7.5% PEG | 3% sucrose<br>10% PEG | 6.32% sucrose<br>10% PEG | 11.41% sucrose<br>6.25% PEG | 13.07% sucrose |

TABLE 5-continued

Medium osmotic treatments for culturing white spruce somatic embryos.

| Treatment | Week 1<br>290 mmol/kg<br>20 μM ABA | Week 2<br>338 mmol/kg<br>30 μM ABA | Week 3<br>380 mmol/kg<br>30 μM ABA | Week 4<br>508 mmol/kg<br>40 μM ABA | Week 5<br>508 mmol/kg<br>40 μM ABA |
|---|---|---|---|---|---|
| 5 | 3% sucrose<br>7.5% PEG | 3% sucrose<br>10% PEG | 3% sucrose<br>6.75% lactose | 3% sucrose<br>10.07% lactose | 3% sucrose<br>10.07% lactose |

Each treatment comprised nine replicates. The number of embryos per treatment were scored and means prepared. Results are shown in FIG. 2. It can be seen that PEG as the control yielded the highest maturation frequency. The trend was that as PEG was replaced by permeating osmotica, the maturation frequency declined slightly. The earlier that the PEG was replaced, the lower the maturation frequency. Even a small addition of lactose at the third week led to a slight decline (treatment 2) similar to completely replacing PEG with sucrose from this point (treatment 3). Thus, it seems that the earlier PEG is replaced with permeating osmotica, the lower the maturation frequencies obtained. There appears to be no beneficial effect on maturation frequency for spruce of replacing or combining non-permeating water stress with a permeating osmoticum during development. Effects on subsequent germination and growth are more pronounced, as shown in Example 8.

EXAMPLE 7

Raising ABA and Water Stress at the Start of Maturation of White Spruce Somatic Embryos Experiments were established to determine whether increasing ABA and water stress can be applied early in maturation. Somatic embryos in liquid maintenance suspension culture were transferred to liquid culture medium containing 1/20 of the strength of hormones in the preculture medium for 7 days. Seven treatments were prepared using these cultures as outlined below.

TABLE 6

Timing of ABA and PEG application and final ABA concentrations and water potentials of liquid maturation treatments

| Treatment | ABA (μM) | PEG added (%) | Final ABA (μM) | Final water potential (mmol/kg) |
|---|---|---|---|---|
| 1 control | 0 | 0 | 0 | 112 |
| 2 | 5 added day 0 | 0 | 5 | 112 |
| 3 | 5 added day 0 | 5 added day 0 | 5 | 166 |
| 4 | 5 added day 3 | 5 added day 3 | 5 | 166 |
| 5 | 5 added day 5 | 5 added day 5 | 5 | 166 |
| 6 | 10 added day 0 | 7.5 added day 0 | 10 | 216 |
| 7 | 5 added day 0<br>5 added day 3 | 5 added day 0<br>2.5 added day 3 | 10 | 216 |
| 8 | 5 added day 3<br>5 added day 5 | 5 added day 3<br>5 added day 5 | 10 | 216 |
| 9 | 5 added day 0<br>5 added day 3<br>5 added day 5 | 5 added day 0<br>2.5 added day 3<br>1.25 added day 5 | 15 | 239 |

Starting water potential was 112 mmol/kg, and all pre-culture media contained 1/20 strength 2,4-D and BA that were present in the proliferation medium. Following these treatments, a 20% suspension was prepared and the embryos were plated onto solidified maturation medium containing PEG adjusted to 290 mmol/kg with PEG and 20 μM ABA.

Experiments were repeated at least three times and three replicates were prepared per treatment. Cultures were transferred to fresh medium every two weeks. Alternatively, to determine if PEG/ABA liquid maturation treatments modified the optimal starting water potential, the embryos were plated from the nine treatments to medium containing ABA at 20 μM and PEG at 290 or 380 mmol/kg. Additionally, to determine if PEG/ABA liquid maturation treatments modified the optimal starting ABA concentration, the embryos were plated from the nine treatments to medium containing PEG at 337 mmol/kg and ABA at 20 or 40 μM. Cultures were transferred to fresh medium every two weeks. After six weeks, the number of embryos developing per 0.75 mL starting inoculum was recorded. Results are shown in FIGS. 3 and 4. It can be seen from FIG. 3 that all treatments in which PEG and ABA were added gave an improvement over the control. Previous experiments had shown that the control (1/20 of the hormones present in the proliferation medium) yielded almost four times the number of mature embryos compared to no pretreatment (i e., full hormone treatment), and almost three times the number of mature embryos compared to culture in hormone-free preculture medium (i e., means of 154, 41, and 58 mature embryos per replicate, respectively). PEG alone without ABA was generally detrimental. The best treatments were those that contained additions of both PEG and ABA. Adding PEG and ABA commencing after three days of reduced-hormone treatment was preferable to adding them at day 0. Adding PEG and ABA in several steps at days 3 and 5 (treatment 8) was preferable to adding them at day 0. This gave almost a three-fold increase in the number of embryos produced per 0.75 mL of inoculum, producing on average about 224 mature embryos per replicate. This equates to over 280 embryos per milliliter of starting inoculum. Adding PEG and ABA during the liquid culture stage did not influence the optimum water potential of the initial solidified maturation medium which remained at 290 mmol/kg. FIG. 4 shows that, for the optimal liquid treatments, the best starting concentration of ABA was 20 μM. Thus, preculture with ABA and PEG did not eliminate the sensitivity to PEG and ABA following transfer to solidified medium during early stages. Thus, 20 μM ABA and water potential of 290 mmol/kg remained the optimal concentrations following liquid preculture, even when maturation commenced in a liquid culture stage in which ABA and water stress were gradually rising. It is therefore advantageous to start the maturation at some point during the liquid stage by adding ABA and/or water stress, such as PEG, to the medium. Such treatments further improve embryo frequencies and reduce subsequent proliferation of tissues that otherwise may occur.

EXAMPLE 8

Germination of White Spruce Somatic Embryos

Somatic embryos were produced following the methods described in Example 4. Somatic embryos were matured for five to six weeks on PEG medium at a water potential of 290 mmol/kg and containing 20 μM ABA for two weeks, then transferred: to fresh medium with the same concentrations every two weeks (treatment 3), or transferred to medium containing 400 mmol/kg PEG plus 30 μM ABA for two weeks, then transferred to medium containing either 400 mmol/kg PEG plus 40 μM ABA (i e., treatment 5), or to 540 mmol/kg PEG plus 40 μM ABA (i e., treatment 6). Embryos were then desiccated at 4° C. and ambient relative humidity (45%) for two weeks, then placed on germination medium. One batch of desiccated spruce embryos produced using these methods was measured and a moisture content of about 7.7 (±0.2)% recorded. After rehydration, selected somatic embryos were removed to fresh medium. Two weeks after imbibition, the somatic plantlets were removed from the culture medium and their lengths were measured. Between 53 to 63 somatic plantlets were recorded per treatment. Results are shown in Table 7.

TABLE 7

Effect of water stress and ABA concentration on somatic seedling length after desiccation and germination for 14 days.

| | Treatment | | | | | |
|---|---|---|---|---|---|---|
| | 3 | | 5 | | 6 | |
| | water potential mmol/kg | ABA μM | water potential mmol/kg | ABA μM | water potential mmol/kg | ABA μM |
| Week | | | | | | |
| 0–2 | 290 | 20 | 290 | 20 | 290 | 20 |
| 2–4 | 290 | 20 | 400 | 30 | 400 | 30 |
| 4–6 | 290 | 20 | 400 | 40 | 540 | 40 |
| Mean Plantlet Length ± SE (mm) | 11.87 ± 4.45 | | 18.2 ± 3.4 | | 17.6 ± 4.0 | |

Thus, it can be seen that increasing ABA and PEG led to significant increases in plantlet vigor after two weeks compared to the control. In fact, raising ABA to 40 μM and the water potential to 400 or 540 mmol/kg with PEG led to about a 50% increase in plantlet length.

White spruce somatic embryos were produced using all treatments described in Example 6 (replacement of PEG with sucrose or lactose). Embryos of all treatments looked similar, and embryos looked to be of high quality and no greening was evident; however, embryos of treatments 4 and 5 had very slight splitting of the root cap region, suggesting early germination. Embryos were desiccated for two weeks, then rehydrated and visually selected for subsequent transfer to fresh medium. The embryos from all treatments germinated to produce root and epicotyl elongation (i e., 100% germination). Subsequent growth differed amongst the treatments. After four to five weeks growth, 87% of somatic seedlings from treatment 1 had visible new shoot growth (new needles). All other treatments had much lower shoot emergence frequencies. These data shown in Table 8 are based upon a total of 4,783 germinated somatic seedlings.

TABLE 8

Effect of replacing PEG with alternative osmotica at similar osmotic potentials on shoot development frequencies of somatic seedlings of white spruce recorded after 4–5 weeks growth.

| Treatment 1 PEG control | Treatment 2 6.6% lactose, partial PEG replacement | Treatment 3 10% lactose, mid replacement | Treatment 4 13% sucrose mid replacement | Treatment 5 10% lactose early replacement |
|---|---|---|---|---|
| 87.0% | 1.5% | 76.5% | 1.6% | 49.2% |

No benefit was obtained from replacing PEG with alternative osmotica in the middle of development. It can be seen that in addition to reducing maturation frequencies, all permeating osmotica treatments suppressed the rate at which new needles developed. Mixing permeating (lactose) and non-permeating osmotica suppressed shoot development, more seriously than replacing PEG completely with lactose. Replacing PEG with lactose in the middle of development had less of a detrimental effect than replacing it early in development. Maintaining a substantially non-permeating water stress throughout development led to the most vigorous germination and plant growth. Thus, if replacement of PEG is desired, it should occur in the middle or even later in development and should preferably be done rapidly, such as in one step, rather than gradually, preferably after meristems and cotyledons have commenced formation. Where possible, mixing of permeating and non-permeating osmotica (particularly well-metabolised sugars) should be avoided, except for the purpose of providing the desired level of sugar and other nutrients.

In another experiment, somatic embryos from treatment 1 (i e., the PEG control treatment to which reference is made in Table 8) were rehydrated on germination medium for 5 days, at 4° C. to inhibit elongation. They were then transferred to sugar-free germination medium at 20° C. and dark for 7 days, then to low light for a further 10 days, and finally transferred to high light. Six weeks after imbibition, 16% (8/50) of the embryos had converted to seedlings with root and needles, compared to 92% (46/50) for the control. This frequency increased to over 90% by increasing the cold imbibition treatment to 21 days. In the latter case, the somatic embryos had shown some elongation, but were less than 1 cm in length. Embryos germinated on sugar-free medium appeared more light sensitive than somatic embryos grown on medium containing 2% sucrose, and so benefitted from the extended dark period.

In another experiment, white spruce somatic embryos were transferred through the 1/20 hormone increasing PEG/ABA liquid maturation culture (Example 7, treatment 8), then plated onto 20–40 μM ABA, 290–540 mmol/kg PEG transfer schedule (Example 4, treatment 6) followed by desiccation at 4° C. 203 embryos were selected and germinated at 4–12° C. for 4 weeks and produced roots and shoots with needles at a frequency of 191/203=94%. White spruce somatic seedlings produced subsequently using these methods survived transfer to soil in a greenhouse and underwent continued growth at frequencies of 95–100%. However, prolonging maturation of cotyledonary embryos in the presence of high water stress and ABA was detrimental to germination. Thus, after seven to eight weeks of culture of spruce somatic embryos the germination vigour (seedling elongation) and frequencies decreased. Late stage water stress of mid to late cotyledonary stage embryos to below about 30–40% moisture content preferably should not be carried out in the presence of a replenishing source of ABA. This will presumably prevent build up of endogenous ABA, and allow endogenous ABA levels to naturally decline.

EXAMPLE 9

Effect of Reducing ABA Levels During Somatic Embryo Development.

Experiments were conducted to determine the effects of decreasing ABA levels in combination with increasing water stress on development, desiccation tolerance and germination of white spruce. Embryos from preculture (Example 7, treatment 8) were plated onto the transfer schedule outlined below.

TABLE 9

Medium water potential and ABA concentration used in development media for white spruce

| Week | PEG water potential mmol/kg | ABA concentration μM |
|---|---|---|
| 0–2 | 290 | 40 |
| 2–4 | 400 | 20 |
| 5 | 540 | 10 |
| 6 | 540 | 0 |

Thus, the concentration of PEG increased significantly during development while the concentration of ABA decreased. Cotyledonary embryos were visible after the second week of culture, and cotyledons were prominent from the fourth week during which time the somatic embryos were in contact with 40 to 20 μM of ABA. Despite such high water potentials, slight swelling and slight greening of many of the developed embryos was evident, showing early precocious germination. For germination, the best embryos which were not showing precocious germination were selected. Somatic embryos were either germinated directly or were desiccated then germinated as described above. Controls were prepared using embryos developed using pretreatment 8, in Example 7, followed by culture on solidified medium treatment 6 of Example 4.

Results following 8 weeks growth are shown in the following Table.

TABLE 10

Effect of reducing or increasing ABA, with increasing water stress and desiccation on plant growth.

| Treatment | Survival (%) | Shoot development (%) | Total plant length (mm) |
|---|---|---|---|
| Increasing ABA, desiccated | 100% | 93 | 34.5 |
| Reducing ABA, no desiccation | 100% | 0 | 25.8 |
| Reducing ABA, desiccation | 80.5% | 0 | 8.14 |

It was observed that embryos produced using increasing ABA and water stress and then given secondary desiccation survived and underwent vigorous germination and growth. Non-desiccated embryos germinated well initially, and showed good elongation. Later, however, these plants lost vigour and became vitrified; none had shown new needle development even after 12 weeks of growth. Desiccated embryos following the decreasing ABA did not all survive desiccation, and the majority were very stunted, showing very little elongation. Shoot development again was very poor. Thus, reducing ABA to low levels by the late stage of development appears detrimental to desiccation tolerance, and did not give rise to viable plants. It seems beneficial to maintain ABA at relatively high levels throughout the majority of development, then to preferably further reduce or eliminate ABA levels during further water stressing to low moisture contents below about 30–40% commencing sometime during cotyledonary development and preferably during the late cotyledonary stages.

Western Larch

EXAMPLE 10

Western Larch Somatic Embryogenesis

Western larch was found to be a particularly difficult species for somatic embryogenesis. Somatic embryos cultured in ABA and a mild water stress of 3% sucrose rarely produced mature embryos, the tissue instead showing pronounced proliferation of immature embryos. When embryos of stages later than the globular stage were produced, they were prone to greening very early (within two to three weeks of plating) and germinating precociously before late stages were sufficiently developed. As such, the embryos were not capable of germinating and forming normal somatic plants with functioning root and shoot meristem.

In order to test the effect of increased ABA and osmoticum, somatic embryos were first cultured on ½ LM full hormone proliferation medium, then transferred to hormone-free preculture medium with 3% sucrose for one week prior to plating 0.75 mL of a 20% (w/v) suspension culture onto filter paper supports overlaying solidified maturation medium. The somatic embryos were plated on PEG medium of 330 mmol/kg and 16 μM ABA, then transferred to 380 mmol/kg PEG medium, 24 ABA after 1 week, then transferred to 450 mmol/kg PEG medium, 32 μM ABA after the third week. These were then either desiccated at week 5 or were transferred to 540 mmol/kg PEG, 40 μM ABA for up to two more weeks before desiccating.

It was found that the problem of tissue proliferation was much reduced by using the foregoing protocol. Mature somatic embryos were formed which were inhibited from germinating precociously, even after five to seven weeks of culture. When desiccated and germinated using the same protocol described above for spruce, these produced viable somatic plantlets with root and developing needles.

Douglas Fir

EXAMPLE 11

Douglas Fir Somatic Embryogenesis

The basal medium used for Douglas fir culture (TX medium) is shown below.

A. Major Elements (mg/L Medium)
  $KNO_3$ 950
  $CaCl_2 2H_2O$ 211
  $MgSO_4 \cdot 7H_2O$ 925
  $KH_2PO_4$ 170

B. Micro Elements
  KI 2.075
  $H_3BO_3$ 15.5
  $MnSO_4-H_2O$ 13.85
  $ZnSO_4-7H_2O$ 21.5
  $Na_2MoO_4-2H_2O$ 0.625
  $CuSO_4-5H_2O$ 0.25
  $CoCl_2-6H_2O$ 0.065
  $FeSO_4 \cdot 7H_2O$ 13.7
  Na-EDTA 18.1

C. Vitamins
  Myo-Inositol 50
  Thiamine HCl 0.05
  Pyridoxine-HCl 0.05
  Nicotinic acid 0.25

Douglas fir may be cultured using sucrose at 1–3% (30–90 mM), however, other sugars may be used at the same concentrations. Maintenance cultures usually contain the sugar at about 1%. Maltose or glucose are sugars that have been reported to be superior for some plant species in both the maintenance cultures (Gupta U.S. Pat. No. 5,563,061) and maturation cultures (Uddin U.S. Pat. No. 5,187,092). Douglas fir embryogenic tissue was induced from developing seed. Embryos contained in megametophytes were induced and maintained on TX maintenance medium having 1% sucrose. This medium contained 0.2 g/L glutamine and 0.2 g/L casein hydrolysate. Selected embryogenic tissue was subcultured biweekly per petri dish. Medium was solidified with 2.4 g/L PHYTAGEL™. This medium contained 9 µM 2,4-D and 4.5 µM BA. Liquid suspension cultures were maintained in flasks containing 50 mL liquid maintenance medium Liquid cultures were subcultured weekly. For maturation, the embryogenic suspension was first precultured in liquid medium without growth regulators, and subcultured weekly. The water potential of the maintenance cultures and precultures remained below 150 mmol/kg. After one or two weeks of preculture, 1 to 2 g of filtered tissue was resuspended in 10 mL fresh medium and 0.75 mL of the new suspension was pipetted onto the solid maturation medium. Maturation medium contained calcium chloride at 105 mg/L, and ammonium nitrate was included at 400 mg/L. Glutamine was used at 0.8 g/L for the first week then reduced to 0.1 g/L thereafter. Casein hydrolysate was maintained at 0.2 g/L. The sugar was increased to 2–3% and the medium was solidified with Phytagel at 2.8 to 3.4 g/L. ABA was added into the medium after filter sterilization. The maturation medium also contained PEG. The ABA and water potential were raised following the schedule in the following table.

TABLE 11

ABA and medium water potential for culture of Douglas fir somatic embryos

| week | 1 | 2 | 3 | 4 | 5 | 6 |
|---|---|---|---|---|---|---|
| ABA µM | 30 | 40 | 40 | 40 | 50 | 60 |
| water potential mmol/kg | 294 | 425 | 653 | 653 | 736 | 814 |

In some instances, the PEG was reduced and the water potential made up to the desired level using lactose at 0% in the first week, 1% in week 2, 4% in weeks 3 and 4, 5% in week 5, and 6% in week 6. Although this allowed a firmer gel to set than otherwise would occur with PEG alone, it may not provide any other benefit over full PEG (see, for example, Table 8), particularly if liquid culture medium is used. However, replacing PEG with sucrose or lactose at week 5 or week 6 gave very good results, at least comparable to those obtained with PEG being maintained. The embryos were desiccated and stored in a freezer as described for spruce, or germinated directly without desiccation. For germination, embryos were placed on half-strength basal medium containing 0.4 g/L calcium nitrate, 0.2 g/L ammonium nitrate, no hormones and 2% sucrose and 0.6% agar. These were grown in the light.

The above procedure led to well-developed Douglas fir somatic embryos that matured with high frequency of viability. Precocious germination was prevented and embryos resembling zygotic embryos with large developed cotyledons were formed. These embryos underwent germination, and manifested shoot and needle development at close to 100% frequency. Rooting was very vigorous, and needles developed as early as three weeks after germination. To date, Douglas fir somatic plants produced using the methods of this invention have been transferred to soil in a greenhouse where they survived at a frequency up to 95%, with good continuing growth and vigor.

What is claimed is:

1. A method of producing viable mature conifer cotyledonary desiccation-tolerant somatic embryos, including:
  (i) nourishing the embryos with a suitable metabolizable carbon source, and
  (ii) treating the embryos with at least one growth regulator influencing embryo development selected from the group consisting of abscisic acid, its precursors, derivatives, and analogs, and
  (iii) water stressing the embryos;
    wherein the type, intensity, and duration of the water stressing, and the type and concentration of the metabolizable carbon source and growth regulator are selected to reduce the moisture content of the embryos to a level of less than about 55% and to render the embryos desiccation-tolerant, and wherein the water stressing is non-plasmolysing;
  characterized in that:
    the concentration of the growth regulator is raised from a selected initial concentration to a selected peak concentration value.

2. The method of claim 1, further comprising water stressing the mature somatic embryos to reach a severely desiccated state characterised by a moisture content of less than about 30% to 36% following the completion of the growth regulator treatment.

3. The method of claim 1, wherein the water stressing and growth regulator treatments continue after the embryos attain desiccation tolerance.

4. The method of claim 1, wherein at least one of the water stressing and growth regulator treatments continues after the embryos attain desiccation tolerance.

5. The method of claim 4, wherein the growth regulator treatment continues after the embryos attain desiccation tolerance.

6. The method of claim 1, wherein the temperature is selected to be in the range of about 0° C. to about 35° C.

7. The method of claim 1, wherein at least one of the growth regulator and the water stressing treatments is applied to the embryos before the globular stage.

8. The method of claim 1, wherein at least one of the growth regulator and the water stressing treatments is applied to the embryos before the club-shaped stage.

9. The method of claim 1, wherein the commencement of the growth regulator treatment and the commencement of the water stressing treatment are concurrent.

10. The method of claim 1, wherein the concentration of the growth regulator is selected to be about 0.1 $\mu$M to about 300 $\mu$M.

11. The method of claim 1, wherein the concentration of the growth regulator is raised from a selected initial concentration to a selected peak concentration value before the completion of the growth regulator treatment period.

12. The method of claim 11, wherein the initial concentration of the growth regulator at the commencement of the growth regulator treatment is selected to be less than about 40 $\mu$M.

13. The method of claim 11, wherein the peak concentration of the growth regulator is selected to be about 30 $\mu$M to about 200 $\mu$M.

14. The method of claim 13, wherein the peak concentration of the growth regulator is selected to be about 30 $\mu$M to 100 $\mu$M.

15. The method of claim 1, wherein the completion of the growth regulator treatment comprises the removal of the embryos from the influence of the growth regulator.

16. The method of claim 1, wherein the growth regulator treatment and the water stressing treatment are not completed concurrently.

17. The method of claim 16, wherein the water stressing treatment continues after the completion of the growth regulator treatment.

18. The method of claim 11, wherein the concentration of the growth regulator s raised progressively during at least part of the growth regulator treatment period.

19. The method of claim 18, wherein the concentration of the growth regulator is increased incrementally.

20. The method of claim 19, wherein the incremental increase of the growth regulator is at least about 5% of the initial concentration of the growth regulator.

21. The method of claim 19, wherein the growth regulator is raised from its initial concentration to its peak concentration in a single increment.

22. The method of claim 19, wherein the growth regulator is raised from its initial, concentration to its peak concentration in a series of increments.

23. The method of claim 18, wherein the concentration of the growth regulator does not increase during, the early part of the growth regulator treatment period.

24. The method of claim 20, wherein the concentration of the growth regulator does not increase during the middle part of the growth regulator treatment period.

25. The method of claim 20, wherein the concentration of the growth regulator does not increase during the late part of the growth regulator treatment period.

26. The method of claim 25, wherein there is no net increase or net decrease in the concentration of the growth regulator during the late part of the growth regulator treatment period.

27. The method of claim 1, wherein the means of completing the growth regulator treatment is selected from the class comprising the discontinuation of the growth regulator treatment and the removal of the growth regulator from the embryos' environment.

28. The method of claim 1, wherein the growth regulator treatment is completed before the moisture content of the embryos reaches about 30%.

29. The method of claim 28, wherein the growth regulator treatment is completed before the moisture content of the embryos reaches about 40%.

30. The method of claim 29, wherein the growth regulator treatment is completed before the moisture content of the embryos reaches about 55%.

31. The method of claim 1, wherein the growth regulator treatment is completed before the embryos reach the late cotyledonary stage.

32. By The method of claim 1, wherein the growth regulator treatment is completed when the embryos reach the late cotyledonary stage.

33. The method of claim 1, wherein the growth regulator is supplemented with at least one selected suitable growth promoter selected from the group comprising auxin, cytokinin, gibberellin, and functional equivalents thereof.

34. The method of claim 33, wherein the growth promoters are selected from the group comprising auxin, cytokinin, and functional equivalents thereof.

35. The method of claim 1, wherein the growth regulator is abscisic acid.

36. The method of claim 1, wherein the water stressing creates a water potential of at least about −260 mmol/kg prior to the late cotyledonary stage of development.

37. The method of claim 1, wherein the water stressing creates a water potential of at least about −400 mmol/kg prior to the late cotyledonary stage of development.

38. The method of claim 1, wherein the intensity of the water stressing is raised from a selected initial intensity to a selected higher intensity before the completion of the water stressing period.

39. The method of claim 38, wherein the water stressing creates a water potential of at least about −800 mmol/kg prior to the late cotyledonary stage of development.

40. The method of claim 38, wherein the initial intensity of the water stressing creates a water potential of at least about −120 mmol/kg.

41. The method of claim 1, wherein the water stressing is applied by at least one means selected from the class comprising environmental effects, water stressing agents, and combinations of environmental effects and water stressing agents.

42. The method of claim 22, wherein the water stressing of the embryos to reach a severely desiccated state is selected to reduce the amount of free unbound water to a level sufficient to induce freezing tolerance in the embryos.

43. The method of claim 22, wherein the rate of water loss in water stressing the embryos to reach a severely desiccated state is greater than the rate of water loss in water stressing the embryos to a mature cotyledonary stage.

44. The method of claim 22, wherein the water stressing is applied by at least one means selected from the class comprising environmental effects, water stressing agents, and combinations of environmental effects and water stressing agents.

45. The method of claim 41, wherein the water stressing is applied at least in part by means of at least one gel.

46. The method of claim 44, wherein the water stressing is applied at least in part by means of at least one gel.

47. The method of claim 41, wherein the water stressing is applied at least in part by means of at least one osmoticum.

48. The method of claim 44, wherein the water stressing is applied at least in part by means of at least one osmoticum.

49. The method of claim 47, wherein the water stressing is applied in part by an embryo cell-permeating osmoticum.

50. The method of claim 48, wherein the water stressing is applied in part by an embryo cell-permeating osmoticum.

51. The method of claim 47, wherein at least one osmoticum is selected from the group comprising non-permeating osmotica.

52. The method of claim 48, wherein at least one osmoticum is selected from the group comprising non-permeating osmotica.

53. The method of claim 51, wherein a second osmoticum is present selected from the group comprising permeating osmotica.

54. The method of claim 52, wherein a second osmoticum is present selected from the group comprising permeating osmotica.

55. The method of claim 49, wherein the water stressing is applied at least in part by a concentration of the metabolizable carbon source in excess of that utilized by the embryo for nutrition.

56. The method of claim 50, wherein the water stressing is applied at least in part by a concentration of the metabolizable carbon source in excess of that utilized by the embryo for nutrition.

57. The method of claim 53, wherein the water stressing is applied at least in part by a concentration of the metabolizable carbon source in excess of that utilized by the embryo for nutrition.

58. The method of claim 54, wherein the water stressing is applied at least in part by a concentration of the metabolizable carbon source in excess of that utilized by the embryo for nutrition.

59. The method of claim 51, wherein the osmoticum has a molecular size of at least about 30 Angstrom units (Å).

60. The method of claim 52, wherein the osmoticum has a molecular size of at least about 30 Angstrom units (Å).

61. The method of claim 51, wherein the water stressing agent is selected from the group comprising polyalkylene glycols.

62. The method of claim 52, wherein the water stressing agent is selected from the group comprising polyalkylene glycols.

63. The method of claim 61, wherein the water stressing agent comprises at least one polyalkylene glycol having a minimum molecular weight of about 1,000.

64. The method of claim 62, wherein the water stressing agent comprises at least one polyalkylene glycol having a minimum molecular weight of about 1,000.

65. The method of claim 41, wherein the environmental water stressing is applied at least in part by relative humidity of less than 100%.

66. The method of claim 44, wherein the environmental water stressing is applied at least in part by relative humidity of less than 100%.

67. The method of claim 65, wherein the water stressing is applied at least in part by a controlled decrease in relative humidity.

68. The method of claim 66, wherein the water stressing is applied at least in part by a controlled decrease in relative humidity.

69. The method of claim 1, wherein there is a net increase in the intensity of water stressing of the embryos over the duration of the water stressing treatment period.

70. The method of claim 69, wherein the net increase in the intensity of water stressing of the embryos is effected by changing the value of the water potential from a selected initial value to a selected final value.

71. The method of claim 1, wherein the embryos are cultured in a bioreactor.

72. The method of claim 1, wherein the embryos are in contact with medium with which is associated toxin removal means, said means being selected from the group comprising adsorbent means and filtration means.

73. The method of claim 72, wherein the adsorbent means comprises activated charcoal.

74. The method of claim 73, wherein the activated charcoal is pre-saturated with the growth regulator.

75. The method of claim 72, wherein the filtration means is selected from the group comprising molecular sieves and dialysis.

76. The method of claim 1, further comprising culturing the embryos in a medium containing at least one of:
  (i) auxin, or a functional equivalent thereof in the amount of 0 $\mu$M up to about 9 $\mu$M;
  (ii) cytokinin, or a functional equivalent thereof, in the amount of 0 $\mu$M up to about 4.5 $\mu$M.

77. The method of claim 76, further comprising water stressing the immature embryos to create a water potential of at least about −40 mmol/kg.

78. The method of claims 2, wherein the somatic embryos are frozen following the water stressing treatment.

79. The method of claim 1, wherein the embryos are in contact with medium.

80. The method of claim 79, wherein the embryos are removed from medium after they have attained a moisture content of about 55%.

81. The method of claim 2, wherein the embryos are in contact with medium during water stressing of the embryos to reach a severely desiccated state.

82. The method of claim 1, wherein the embryos are supported by nutrient-permeable support means in contact with a medium.

83. The method of claim 82, wherein the embryos are removed from contact with the support means after the embryos have attained a moisture content of about 55%.

84. The method of claim 2, wherein the embryos are supported by nutrient-permeable support means in contact with a medium during water stressing of the embryos to reach a severely desiccated state.

85. The method of claim 1, further comprising rehydrating the mature embryos in preparation for germination.

86. The method of claim 85, further comprising imbibing the embryos in 0–15° C.

87. The method of claim 85, wherein the rehydrating step occurs following a rest period following termination of water stressing the embryos.

88. The method of claim 1, further comprising imbibing the mature embryos in medium containing a suitable carbon source.

89. The method of claim 88, further comprising germinating the imbibed embryos in the absence of a nutritive carbon source.

90. The method of claim 1, further comprising germinating the mature embryos to form somatic seedlings.

91. A method of producing viable mature conifer cotyledonary desiccation-tolerant somatic embryos, including:
  (i) nourishing the embryos with a suitable metabolizable carbon source, and
  (ii) treating the embryos with at least one growth regulator influencing embryo development selected from the group consisting of abscisic acid, its precursors, derivatives, and analogs, and (iii) water stressing the embryos; wherein the type, intensity, and duration of the water stressing, and the type and concentration of the metabolizable carbon source and growth regulator are selected to reduce the moisture content of the embryos to a level of less than about 55% and to render the embryos desiccation-tolerant, and wherein the water stressing is non-plasmolysing;

characterized in that:
(a) the concentration of the growth regulator is raised from a selected initial concentration to a selected peak concentration value, and
(b) the intensity of the water stressing is raised from a selected initial intensity to a selected higher intensity.

92. The method of claim 91, further comprising water stressing the mature somatic embryos to reach a severely desiccated state characterised by a moisture content of less than about 30% to 36% following the completion of the growth regulator treatment.

93. A method of producing viable mature conifer cotyledonary desiccation-tolerant somatic embryos, including:
(i) nourishing the embryos with a suitable metabolizable carbon source, and
(ii) treating the embryos with at least one growth regulator influencing embryo development selected from the group consisting of abscisic acid, its precursors, derivatives, and analogs, and
(iii) water stressing the embryos; wherein the type, intensity, and duration of the water stressing, and the type and concentration of the metabolizable carbon source and growth regulator are selected to reduce the moisture content of the embryos to a level of less than about 55% and to render the embryos desiccation-tolerant, and wherein the water stressing is non-plasmolysing;

characterized in that:
(a) the concentration of the growth regulator is raised from a selected initial concentration to a selected peak concentration value, and
(b) the intensity of the water stressing over the water stressing treatment period is selected to be at least at its initial level.

94. The method of claim 93, further comprising water stressing the mature somatic embryos to reach a severely desiccated state characterised by a moisture content of less than about 30% to 36% following the completion of the growth regulator treatment.

* * * * *